(12) United States Patent
Hu et al.

(10) Patent No.: US 12,419,875 B2
(45) Date of Patent: Sep. 23, 2025

(54) USE OF AXITINIB AND ANALOGS THEREOF IN PREPARING BLOOD-BRAIN BARRIER PERMEABILITY REGULATOR

(71) Applicant: ZHEJIANG UNIVERSITY, Hangzhou (CN)

(72) Inventors: Fuqiang Hu, Hangzhou (CN); Lijuan Wen, Hangzhou (CN); Hong Yuan, Hangzhou (CN); Kai Wang, Hangzhou (CN); Tingting Meng, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1070 days.

(21) Appl. No.: 17/418,574

(22) PCT Filed: Jul. 9, 2019

(86) PCT No.: PCT/CN2019/095242
§ 371 (c)(1),
(2) Date: Jun. 25, 2021

(87) PCT Pub. No.: WO2020/134022
PCT Pub. Date: Jul. 2, 2020

(65) Prior Publication Data
US 2022/0079929 A1    Mar. 17, 2022

(30) Foreign Application Priority Data
Dec. 27, 2018    (CN) .......................... 201811610364.6

(51) Int. Cl.
*A61K 31/4439*    (2006.01)
*A61P 25/16*    (2006.01)

(52) U.S. Cl.
CPC .......... *A61K 31/4439* (2013.01); *A61P 25/16* (2018.01)

(58) Field of Classification Search
CPC .... A61K 31/337; A61K 47/64; A61K 31/352; A61K 31/713; A61K 31/4439; A61P 35/00; A61P 25/16
See application file for complete search history.

(56) References Cited

U.S. PATENT DOCUMENTS

2014/0294726 A1*  10/2014  Jefferies ............... A61K 31/551
                                                                    424/9.1
2016/0222100 A1*   8/2016  Monje-Deisseroth ......................
                                                                   A61K 31/12
2019/0255054 A1*   8/2019  Saiyed ................... A61K 31/69

FOREIGN PATENT DOCUMENTS

CN        102406648 A       4/2012
CN        105816461 A       8/2016

OTHER PUBLICATIONS

Hu-Lowe et al., "Nonclinical Antiangiogenesis and Antitumor Activities of Axitinib (AG-013736), an Oral, Potent, and Selective Inhibitor of Vascular Endothelial Growth Factor Receptor Tyrosine Kinases 1, 2, 3," Clin Cancer Res 2008; 14(22) Nov. 15, 2008. (Year: 2008).*
Hoh et al., "Intermittent dosing of axitinib combined with chemotherapy is supported by 18FLT-PET in gastrointestinal tumours," British Journal of Cancer (2014) 110, 875-881. (Year: 2014).*
Jalota et al., "A drug combination targeting hypoxia induced chemoresistance and stemness in glioma cells," Oncotarget, 2018, vol. 9, (No. 26) pp. 18351-18366. (Year: 2018).*
Ali, N., et al., "Resolution of a Debilitating Paraneoplastic Parkinson-like Neurological Syndrome Following Tyrosine Inhibitor Therapy and Consolidative Nephrectomy in a Patient with Advanced Clear Cell Renal Cell Carcinoma", Urology Case Reports 14 (2017), Jun. 19, 2017, p. 18-20.
Gaelzer, M.M., et al., "Phosphatidylinositol 3-Kinase/AKT Pathway Inhibition by Doxazosin Promotes Glioblastoma Cells Death, Upregulation of p53 and Triggers Low Neurotoxicity", PLOS ONE, Apr. 28, 2016, p. 1-18, vol. 4, No. 11.
International Search Report dated Oct. 16, 2019, issued in PCT/CN2019/095242, 2 pages.
Jun, Z., et al., "Advance of the targeted anti-tumor drugs with samll molecule compounds", J. Int. Oncol., Mar. 2012, p. 172-175, vol. 39, No. 3, with English Language abstract.
Lei, L., "The Research for Anti-Tumor Activity of Axitinib to Gioblastoma and Glioma Stem Cell", A Dissertation for MD Degree, Fudan University, Jan. 15, 2016, p. 4, with Partial English Language translation.
Wen, L., et al., "VEGF-mediated tight junctions pathological fenestration enhances doxorubicin-loaded glycolipid-like nanoparticles traversing BBB for glioblastoma-targeting therapy", Drug Delivery, Nov. 28, 2017, p. 1843-1855, vol. 1, No. 24.
Atochina-Vasserman, E. N., et al., "Pharmacological targeting of VEGFR signaling with axitinib inhibits Tsc2-null lesion growth in the mouse model of lymphangioleiomyomatosis", Am J Physiol Lung Cell Mol Physiol, First published Oct. 2, 2015 309: L1447-L1454.

(Continued)

*Primary Examiner* — Jared Barsky
(74) *Attorney, Agent, or Firm* — Scully, Scott, Murphy & Presser, P.C.

(57) ABSTRACT

The present invention relates to a use of Axitinib and analogs thereof in the preparation of a blood-brain barrier permeability regulator. The blood-brain barrier permeability regulator can reduce blood-brain barrier permeability, and promote recovery of a blood-brain barrier function from a pathologically impaired state to a state close to a physiological barrier. Axitinib and an analog thereof reduce blood-brain barrier permeability by inhibiting the vascular endothelial cell growth factor-phosphatidylinositol kinase-protein kinase B signaling pathway and reducing the degree to which a blood-brain barrier tight junction protein Claudin-5/Occludin is down-regulated. The blood-brain barrier permeability regulator can be used in the treatment of a disease related to causing a change in blood-brain barrier permeability.

6 Claims, 16 Drawing Sheets

(56) References Cited

OTHER PUBLICATIONS

Biron, K. E., et al., "Amyloid Triggers Extensive Cerebral Angiogenesis Causing Blood Brain Barrier Permeability and Hypervascularity in Alzheimer's Disease", PLoS ONE, Aug. 2011, 10 pages, vol. 6, Issue 8.
Keaney, J., et al., "Autoregulated paracellular clearance of amyloid-b across the blood-brain barrier", Sci. Adv., Sep. 18, 2015, 12 pages.
Ma, J., et al. "Dominant Effect of Antiangiogenesis in Combination Therapy Involving Cyclophosphamide and Axitinib", Clin Cancer Res Jan. 15, 2009, 11 pages, 15(2).
Rini, B. I., et al., "Phase II Study of Axitinib in Sorafenib-Refractory Metastatic Renal Cell Carcinoma", Journal of Clinical Oncology, Sep. 20, 2009, 7 pages, vol. 27, No. 27.
Rugo, H. S., et al., "Phase I Trial of the Oral Antiangiogenesis Agent AG-013736 in Patients With Advanced Solid Tumors: Pharmacokinetic and Clinical Results", Journal of Clinical Oncology, Aug. 20, 2005, 10 pages, vol. 23, No. 24.

\* cited by examiner

USE OF AXITINIB AND ANALOGS THEREOF IN PREPARING BLOOD-BRAIN BARRIER PERMEABILITY REGULATOR

TECHNICAL FIELD

The present invention belongs to the field of pharmaceuticals, and relates to a therapeutic use of Axitinib and analogs thereof, in particular to the use of Axitinib and analogs thereof in the preparation of a blood-brain barrier permeability regulator. The blood-brain barrier permeability regulator is useful in treating a disease related to inducing of a change in blood-brain barrier permeability.

BACKGROUND OF THE INVENTION

The blood-brain barrier, a special system for protecting and maintaining functions of the central nervous system, is mainly composed of brain microvascular endothelial cells, tight junctions between endothelial cells, basal lamina and glial cell podocytic process around capillaries, wherein the endothelial cells and tight junctions thereof are important morphological basis for the blood-brain barrier. Most macromolecular substances and more than 98% of small molecule drugs cannot leak through the blood-brain barrier, and only a small part of nutrients with a molecular weight of less than 500 Da can passively diffuse or selectively cross the blood-brain barrier to maintain physiological balance of the central nervous system.

Loss of integrity of the blood-brain barrier is a significant pathological feature in occurrence and development of brain diseases. Brain capillary endothelial cells and the tight junctions expressed between the cells contribute to properties of low-osmotic and high-resistance of the blood-brain barrier. Among others, Claudin-5, Occludin are key proteins forming the tight junctions, and play an important role in maintaining integrity of the blood-brain barrier. Pathological impairment of the blood-brain barrier structure mainly means loss of structural integrity of the tight junction and dysfunction of the barrier, accompanied by down-regulated expression of the tight junction proteins, increased blood-brain barrier permeability, and broken balance of internal environmental of the central nervous system, which is a prominent pathological feature of various central nervous system disease, including glioma, Parkinson's disease, cerebral ischemia, Alzheimer's disease, multiple sclerosis and the like.

Axitinib is a multi-targeted tyrosine kinase inhibitor developed by Pfizer Inc, in the USA which can block autophosphorylation of vascular endothelial growth factor receptor (VEGFR), viability of vascular endothelial growth factor (VEGF) to regulate endothelial cell, microtubule formation and downstream signals. This drug was approved by the Food and Drug Administration (FDA) for marketing on Jan. 27, 2012 with a trade name of Inlyta. This drug is in a form of tablet, and is mainly for treating advanced kidney cancer that does not respond to medicine(s). Axitinib has a Chinese chemical name of N-methyl-2-((2-(((1E)-2-(pyridin-2-yl)ethylene)-1H-indol-6-yl)thio)benzamide, an English chemical name of N-methyl-2-((3-((1E)-2-(pyridine-2-yl) ethenyl)-1H-indazol-6-yl) sulfanyl)benzamide, a molecular formula of $C_{22}H_{18}N_4OS$, a molecular weight of 386.47, and a CAS registration number of 319460-85-0.

An Axitinib analog mainly means an inhibitor which has an action mechanism similar to Axitinib, and may act on the vascular endothelial growth factor-phosphatidylinositol kinase-protein kinase B (VEGF-PI3K-AKT) signaling pathway, which includes, but is not limited to inhibitors involving the sites of VEGF, PI3K, AKT, or the like, such as phosphatidylinositol kinase (PI3K) site inhibitor LY294002.

Recent studies have found that Axitinib has an effect in the treatment of non-small cell lung cancer and leukemia. In addition, it has been further found that Axitinib may resist symptoms of obesity and insensitivity to insulin induced by high-fat diet by promoting browning of white fat cells, and meanwhile has an effect in the treatment of fatty liver. However, the role of Axitinib and analogs thereof in regulating permeability of the blood-brain barrier has not yet been reported.

SUMMARY OF THE INVENTION

The object of the present invention is to provide a use of Axitinib and analogs thereof in the preparation of a blood-brain barrier permeability regulator.

After a thorough research, the present inventors have found that Axitinib and analogs thereof have a regulating effect on permeability of the blood-brain barrier, which can reduce permeability of the blood-brain barrier and promote recovery of a blood-brain barrier function from a pathologically impaired state to a state close to a physiological barrier, and thereby realize the treatment of a disease related to inducing of a change in blood-brain barrier permeability. On the basis of the above findings, the present invention has been accomplished.

In particular, the present invention relates to the followings.

1. Use of Axitinib and an analog thereof in the preparation a blood-brain barrier permeability regulator.

2. The use of item 1, characterized in that the blood-brain barrier permeability regulator is capable of reducing blood-brain barrier permeability and promoting recovery of a blood-brain barrier function from a pathologically impaired state to a state close to a physiological barrier.

3. The use of item 1 or 2, characterized in that the Axitinib and an analog thereof reduce blood-brain barrier permeability by reducing the degree to which a pathological blood-brain barrier tight junction protein Claudin-5/Occludin is down-regulated.

4. The use of item 1 or 2, characterized in that the Axitinib and an analog thereof reduce blood-brain barrier permeability by inhibiting a vascular endothelial cell growth factor-phosphatidylinositol kinase-protein kinase B signaling pathway and reducing the degree to which a blood-brain barrier tight junction protein Claudin-5/Occludin is down-regulated.

5. The use of item 1 or 2, characterized in that the Axitinib analog is an inhibitor which is capable of inhibiting vascular endothelial growth factor, phosphatidylinositol kinase or protein kinase B at any site in a vascular endothelial growth factor-phosphatidylinositol kinase-protein kinase B signaling pathway.

6. The use of item 5, characterized in that the Axitinib analog is a phosphatidylinositol kinase inhibitor.

7. The use of item 1 or 2, characterized in that the blood-brain barrier permeability regulator is a drug for treating a disease related to causing a change in blood-brain barrier permeability.

Effect of the Invention

The blood-brain barrier permeability regulator of the present invention can reduce blood-brain barrier permeability and promote recovery of a blood-brain barrier function from a pathologically impaired state to a state close to a physiological barrier through regulation of blood-brain barrier permeability by Axitinib and an analog thereof, so as to achieve a therapeutic effect on a disease related to inducing of a change in blood-brain barrier permeability, and has a significantly superior technical effect.

DETAILED DESCRIPTION OF THE INVENTION

Figure 1:
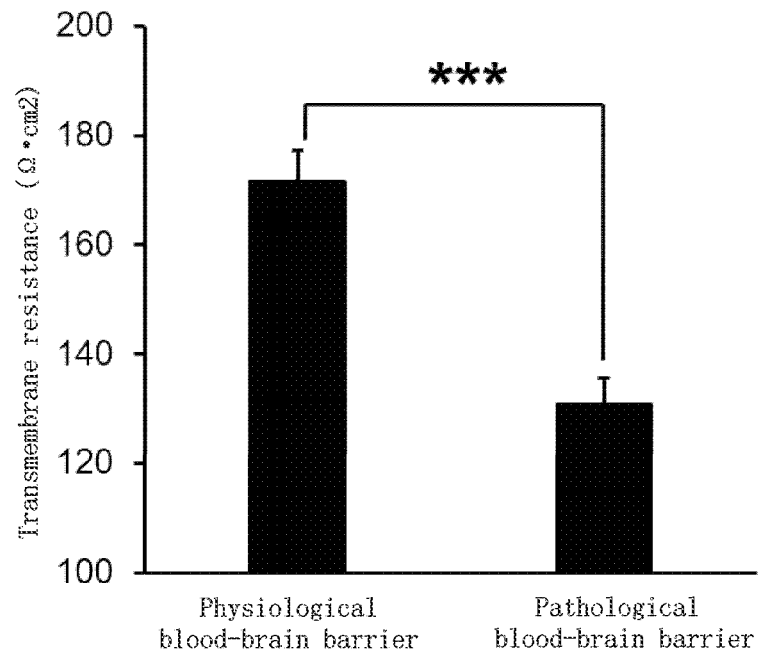
FIG. 1: Determination of transmembrane resistances of a physiological blood-brain barrier and a pathological blood-brain barrier in vitro. A transwell model of brain microvascular endothelial cells bEnd.3 simulates a physiological blood-brain barrier, and a Transwell model of co-incubation of brain microvascular endothelial cells bEnd.3 and glioma cells U87 MG simulates a pathological blood-brain barrier. The results as shown in FIG. 1 are cell transmembrane resistances of physiological blood-brain barrier and pathological blood-brain barrier as detected by a cell resistance meter (n=5).

According to the present invention, Axitinib is a multi-targeted tyrosine kinase inhibitor with a Chinese chemical name of N-methyl-2-((2-((1E)-2-(pyridin-2-yl)ethylene)-1H-indol-6-yl)thio)benzamide; an English chemical name of N-methyl-2-((3-((1E)-2-(pyridine-2-yl)ethenyl)-1H-indazol-6-yl) sulfanyl)benzamide; a molecular formula of $C_{22}H_{18}N_4OS$; and a molecular weight of 386.47; and CAS registration number of 319460-85-0.

According to the present invention, an Axitinib analog means the inhibitors which have a mechanism of action similar to Axitinib, and can act on the vascular endothelial growth factor-phosphatidylinositol kinase-protein kinase B (VEGF-PI3K-AKT) signaling pathway, such as phosphatidylinositol kinase (PI3K) inhibitor LY294002 or the like.

The present inventors have found that Axitinib and analogs thereof have a regulating effect on permeability of the blood-brain barrier, which can reduce permeability of the blood-brain barrier and promote recovery of a blood-brain barrier function from a pathologically impaired state to a state close to a physiological barrier, and thereby realize the treatment of a disease related to inducing of a change in blood-brain barrier permeability.

As a disease related to blood-brain barrier function, glioma, Parkinson's disease, cerebral ischemia, Alzheimer's disease, and multiple sclerosis can be listed. Occurrence of these brain diseases will cause loss of structural integrity of the tight junction and dysfunction of the barrier, accompanied by down-regulated expression of the tight junction proteins, increased blood-brain barrier permeability, and broken balance of internal environmental of the central nervous system.

According to the examples as described below, it is clear that Axitinib and analogs thereof can exert a therapeutic effect on glioma and Parkinson's disease through its regulation of blood-brain barrier permeability.

It has been found in a further research that Axitinib and analogs thereof can block vascular endothelial growth factor receptor (VEGFR), inhibit binding of vascular endothelial growth factor (VEGF) and vascular endothelial growth factor receptor (VEGFR), inhibit the phosphatidylinositol kinase-protein kinase B (PI3K-AKT) protein signaling pathway downstream of VEGF, decrease the down-regulated expression of Claudin-5/Occludin protein, reduce blood-brain barrier permeability, and enable recovery of a blood-brain barrier function from a pathologically impaired state to a state close to a physiological barrier in a dose-dependent manner. It has also been found in this research that Axitinib and analogs thereof can promote recovery of a blood-brain barrier function from a pathologically impaired state to a state close to a physiological barrier, significantly inhibit growth of gliomas, significantly alleviate dyskinesia in Parkinson's disease, and effectively treat glioma and Parkinson's disease. It has also been found in this research that Axitinib and analogs thereof had no significant cytotoxicity to glioma cells and brain endothelial cells under a condition of the drug concentration at which recovery of a blood-brain barrier function from a pathologically impaired state to a state close to a physiological barrier is regulated. It indicates that the therapeutic effect of Axitinib and analogs thereof on glioma and Parkinson's disease is achieved by regulating the decrease in blood-brain barrier permeability and promoting recovery of a blood-brain barrier function from a pathologically impaired state to a state close to a physiological barrier.

In the followings, the present invention will be described in details with reference to Examples and the drawings. It should be noted that the following Examples are merely for illustration only, and do not limit the protection scope of the present invention.

EXAMPLES

Example 1 Growth of Glioma Causes a Pathological Impairment of Blood-Brain Barrier and an Increase in Permeability 1. Construction of a Cell Model of Physiological Blood-Brain Barrier Brain microvascular endothelial cells bEnd.3 were used as model cells of a blood-brain barrier. 0.5 mL suspension of well-grown bEnd.3 cells was inoculated in the chamber of a 12-well Transwell plate with a pore size of 0.4 μm at a cell density of $1 \times 10^5$/well. 1.5 mL of fresh culture medium was supplemented in the outer chamber. The culture medium was refreshed every other day. Incubation was continued for 15 days at 37° C. and 5% $CO_2$. When the cell transmembrane resistance value was greater than 150 ohm·cm$^2$ ($\Omega \cdot cm^2$), a cell model of physiological blood-brain barrier was obtained for evaluation.

2. Construction of a Cell Model of Pathological Blood-Brain Barrier

U87 MG glioma cells were used as brain tumor model cells. 1.5 mL suspension of well-grown U87 MG cell suspension was inoculated in a 12-well plate at a cell density of $2 \times 10^5$/well. Incubation was continued at 37° C. and 5% $CO_2$ until the cells adhere. Then, the physiological blood-brain barrier as constructed by Method 1 in the Example 1, i.e., the Transwell chamber with bEnd.3 cells grown, was transferred to the 12-well plate with U87 MG cells grown. Co-culture was further continued for 24 hours to obtain a cell model of pathological blood-brain barrier.

3. Down-Regulation of the Tight Junction Protein and an Increase in Blood-Brain Barrier Permeability Caused by Growth of Glioma in the Model Cells The physiological blood-brain barrier and the pathological blood-brain barrier as constructed in Method 1 and Method 2 in the Example 1 were used as models, respectively. The Transwell chamber with bEnd.3 cells grown was transferred to another 12-well plate, and was washed with PBS for 3 times. 0.5 mL HBSS nutrient solution was added to the chamber, and the outer chamber was supplemented with 1.5 mL HBSS nutrient solution. The cells were equilibrated at 37° C. for 15 minutes. Transmembrane resistance of the cells was detected with a transmembrane resistance meter. The results were shown in FIG. 1. The physiological blood-brain barrier and the pathological blood-brain barrier as constructed in Method 1 and Method 2 in the Example 1 were used as models, respectively. The Transwell chamber with bEnd.3 cells grown was transferred to another 12-well plate, and was washed for 3 times with PBS. A solution of dextran having a molecular weight of 10 kDa, which is fluorescently-labeled by a FITC-label, in HBSS was added to the chamber, and the outer chamber was supplemented with 1.5 mL HBSS nutrient solution. After the cells were incubated at 37° C. in the dark for 4 hours, concentration of FITC-dextran transferred to the outer chamber via the Transwell chamber was detected with a fluorescence spectrophotometer. The results were shown in FIG. 2. The physiological blood-brain barrier and the pathological blood-brain barrier as constructed in Method 1 and Method 2 in the Example 1 were used as models, respectively. The Transwell chamber with bEnd.3 cells grown was taken out, and washed with PBS for 3 times, then fixed with 4% formaldehyde, and blocked with 10% bovine serum albumin for 30 minutes. Thereafter, Claudin-5/Occludin primary antibody was added, and was incubated at 4° C. overnight, and finally was incubated with fluorescently-labeled secondary antibody for 1 hour. The nucleus was counterstained with DAPI. Expression of tight junction protein of Claudin-5/Occludin was observed with a laser confocal microscope. Expression level of Claudin-5/Occludin was semi-quantitatively analyzed with Image J. The Results were shown in FIG. 3.

Figure 2:
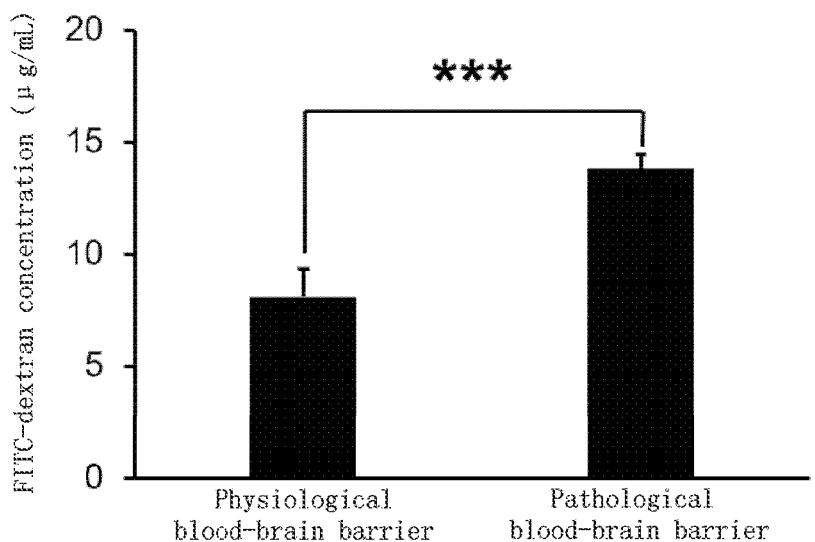
FIG. 2: Translocation efficiency of FITC-dextran across a physiological blood-brain barrier and a pathological blood-brain barrier in vitro. FITC-dextran with a molecular weight of 10 kDa was used to evaluate permeability of the blood-brain barriers. A solution of FITC-dextran in HBSS was added to a Transwell chamber, and was left for 4 hours. The result as shown in FIG. 2 are the FITC-dextran concentrations (n=3) of the Transwell outer chamber as detected by a fluorescence spectrophotometer.
Figure 3:
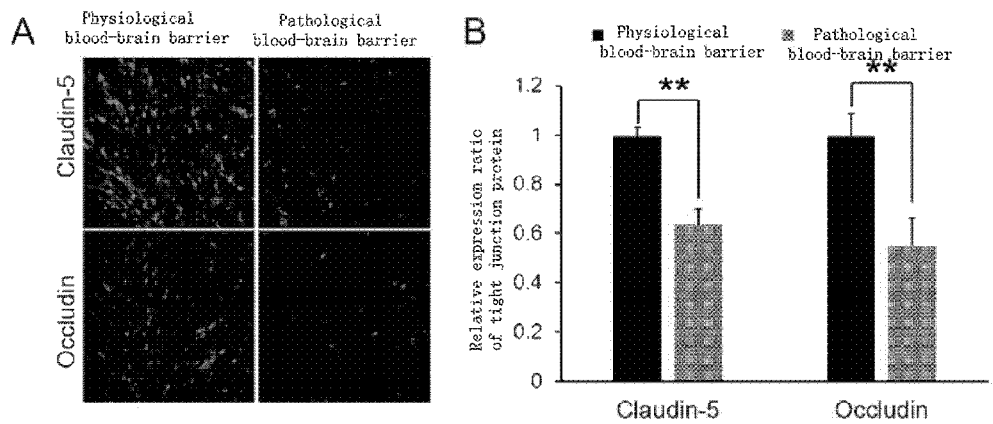
FIG. 3: Claudin-5/Occludin expression of barrier tight junction proteins of a physiological blood-brain barrier and a pathological blood-brain in vitro. A Transwell model of brain microvascular endothelial cells bEnd.3 simulates a physiological blood-brain barrier, and a Transwell model of co-incubation of brain microvascular endothelial cells bEnd.3 and glioma cells U87 MG simulates a pathological blood-brain barrier. Immunofluorescence staining was performed on bEnd.3 cells on the membrane of Transwell chamber. Panel A shows the expression result of a tight junction protein of Claudin-5/Occludin as observed by a confocal microscope. Panel B is the result of fluorescence semi-quantitative analysis of Claudin-5 expression by Image J (n=3).

As can be seen from the results shown in FIGS. 1 to 3, in the pathological blood-brain barrier cell model, after co-incubation of tumor cells U87 MG and bEnd.3 cells, the cell transmembrane resistance was decreased, and as compared with a normal blood-brain barrier model, protein expression of tight junction protein of Claudin-5/Occludin was significantly down-regulated, blood-brain barrier permeability was increased, and transmembrane transport of FITC-dextran was increased.

4. Down-Regulation of Tight Junction Protein and an Increase in Blood-Brain Barrier Permeability Caused by Growth of Glioma Causes in the Model Animals Male BABL/c nude mice (20±2 g) were used as the model animals. U87-luci glioma cells expressing luciferase were inoculated in the striatum area of nude mice at a concentration of $5 \times 10^5$ cells/5 µL by means of a brain stereotaxic instrument (inoculation coordinates, 0.8 mm on the anterior side of bregma, 2 mm on the right side, and 3 mm in depth), to construct an in situ glioma model. After the glioma grew to a suitable volume, a FITC-dextran solution was injected into tail veins. After 4 hours, the intact brain of the nude mice was taken by cardiac perfusion. The tissue was frozen and sectioned. Permeability of FITC-dextran in the cerebral blood vessels was observed with a laser confocal microscope. CD31 was used to specifically fluorescently-label the cerebral blood vessels. The results are shown in FIG. 4.

Figure 4:
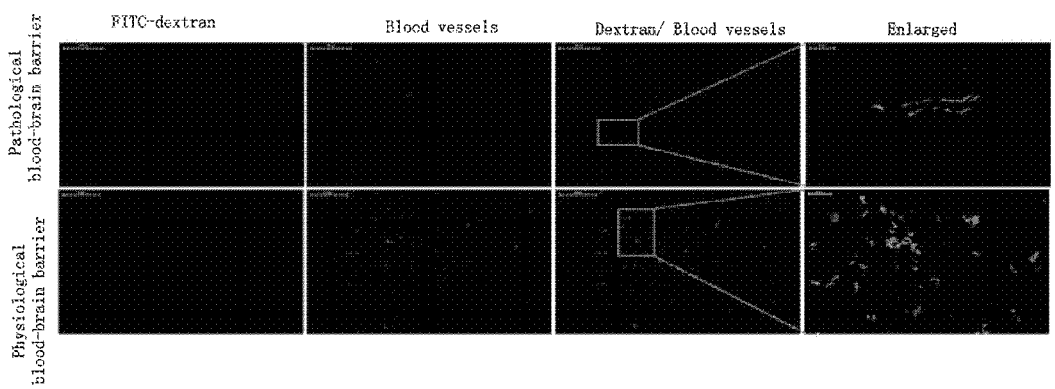
FIG. 4: Evaluation of FITC-dextran permeability in a physiological blood-brain barrier and in a pathological blood-brain barrier in vivo. The model animal was injected with FITC-dextran solution in the tail vein. After 4 hours, samples of a normal brain tissue and a tumor-bearing brain tissue were taken by cardiac perfusion. The thickness of a frozen section of a coronary surface was 5 microns. CD31 (red) was used to specifically label the brain tissue blood vessels. The figures show the results of leakage of FITC-dextran (green) in blood vessels as observed by a laser confocal microscope.

As can be seen from the results shown in FIG. 4, growth of brain tumors will seriously damage the structure of cerebral blood vessels, and blood-brain barrier permeability was increased. As compared with normal brain tissue, in the glioma model, the amount of FITC-dextran permeated from blood vessels was significantly increased.

The intact brains of normal nude mice and in situ glioma tumor-bearing nude mice were taken by cardiac perfusion. Structural changes in blood-brain barrier tight junction protein were observed with a tissue transmission electron microscopy. The results were shown in FIG. 5. Immunofluorescent staining was performed on the tight junction protein of Claudin-5/Occludin of the brain. Expression level of the tight junction protein was observed with a laser confocal microscope. The results were shown in FIG. 6.

Figure 5:
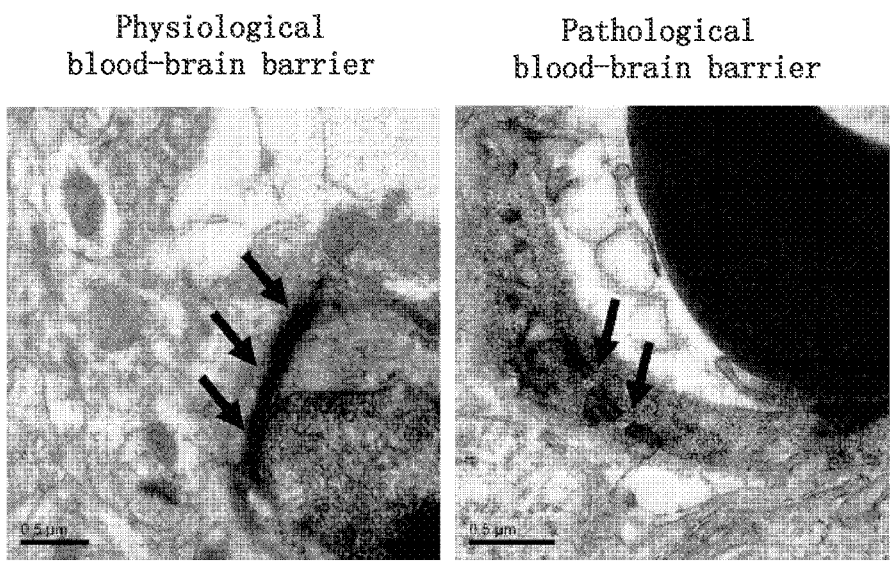
FIG. 5: Tight junction structures of a physiological blood-brain barrier and a pathological blood-brain barrier as observed by transmission electron microscopy at the tissue-level. Samples of a normal brain tissue and a tumor-bearing brain tissue of the model animals were taken by cardiac perfusion. The figure shows the tight junction structure of the blood-brain barrier in the normal brain tissue section (left) and the tight junction structure of the blood-brain barrier in the tumor-bearing brain tissue section (right) as observed by a transmission electron microscope.
Figure 6:
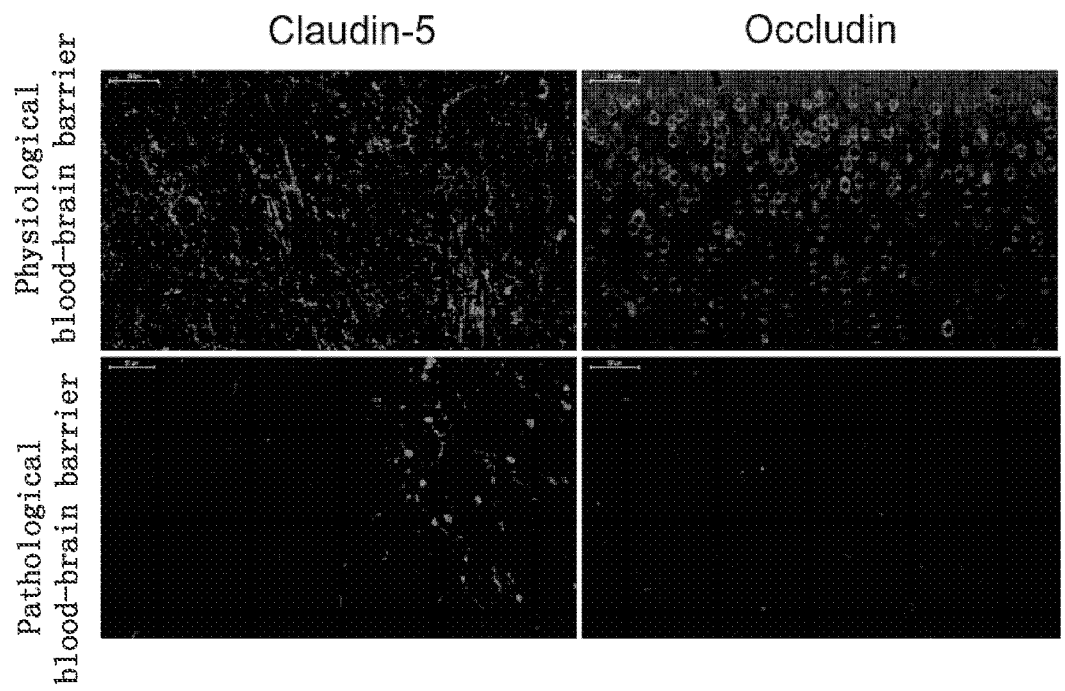
FIG. 6: Claudin-5/Occludin expression of barrier tight junction proteins of a physiological blood-brain barrier and a pathological blood-brain in vitro. Samples of a normal brain tissue and a tumor-bearing brain tissue of the model animals were taken by cardiac perfusion. The thickness of a frozen section of a coronary surface was 5 microns. Immunofluorescence staining was performed on the tight junction protein Claudin-5/Occludin of the brain tissue. The Claudin-5/Occludin expression was observed by a laser confocal microscopy.

As can be seen from the results shown in FIGS. 5 and 6, growth of glioma obviously impaired the tight junction structure of the blood-brain barrier. Expression of tight junction protein in normal brain tissue was complete and continuous, while expression of tight junction protein in the brain tumor tissue was discrete and discontinuous. In addition, growth of glioma significantly down-regulated the expression of tight junction protein of Claudin-5/Occludin, and increased the blood-brain barrier permeability.

Example 2 Axitinib Acts on Vascular Endothelial Growth Factor Receptor (VEGFR) and Blocks the Binding of Vascular Endothelial Cell Growth Factor (VEGF) and Receptor Thereof in a Dose-Dependent Manner The physiological blood-brain barrier as constructed by Method 1 in the Example 1 was used as a model. Exogenous vascular endothelial cell growth factor (VEGF) and Axitinib at different concentrations were added to the Transwell chamber. After the drugs were allowed to act for 24 hours, the Transwell cell with bEnd.3 cells grown was taken out, washed with PBS for three times, fixed with 4% formaldehyde, and blocked with 10% bovine serum albumin for 30 minutes. Thereafter, Claudin-5 primary antibody was added and incubated at 4° C. overnight, and finally was incubated with fluorescently-labeled secondary antibody for 1 hour. The nucleus was counterstained with DAPI. Expression of tight junction protein of Claudin-5 was observed with a laser confocal microscope. The results were shown in FIG. 7.

Figure 7:
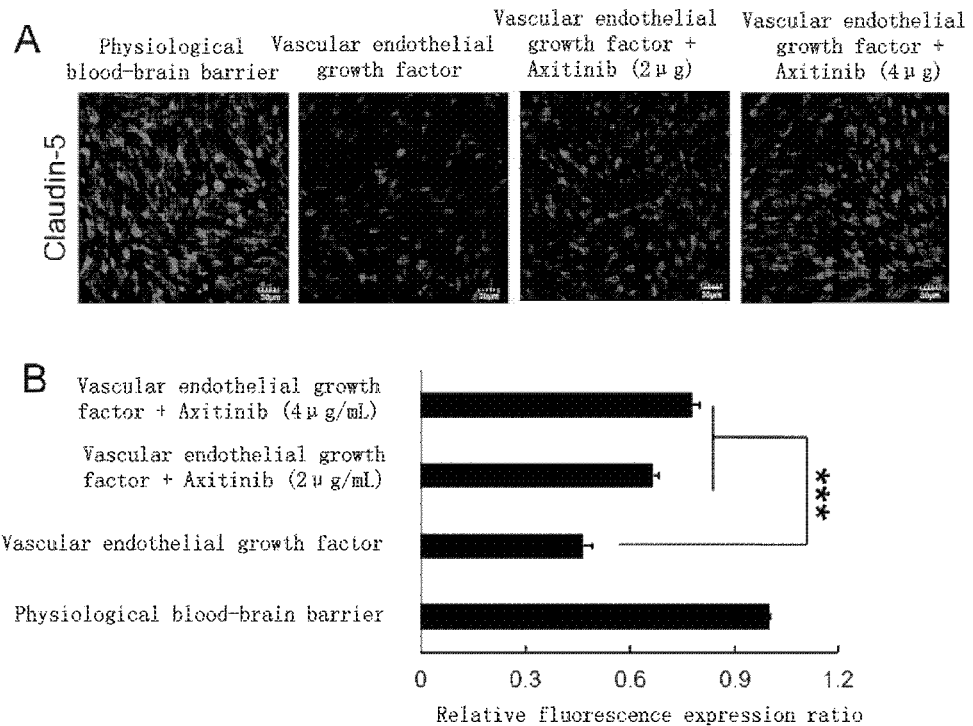
FIG. 7: Dose-dependent blockage of binding of vascular endothelial growth factor (VEGF) and vascular endothelial growth factor receptor (VEGFR) by Axitinib in vitro. A Transwell model of brain microvascular endothelial cells bEnd.3 simulates a physiological blood-brain barrier. Transwell chambers were stimulated with the added exogenous vascular endothelial growth factor (VEGF), and further with Axitinib at different concentrations (0, 2 μg/mL, 4 μg/mL) synergistically for 24 hours. Thereafter, Immunofluorescence staining was performed on bEnd.3 cells on the Transwell chamber membrane. Panel A shows the the expression results of tight junction protein Claudin-5 as observed by a confocal microscope. Panel B is the result of fluorescence semi-quantitative analysis of Claudin-5 expression by Image J (n=3).

As can be seen from the results shown in FIG. 7, Axitinib acts on vascular endothelial cell growth factor receptor (VEGFR), and can block the binding of vascular endothelial cell growth factor (VEGF) and vascular endothelial cell growth factor receptor (VEGFR), and reduce the degree to which Claudin-5 is down-regulated in a dose-dependent manner.

Example 3 Axitinib Blocks the Action Site of Vascular Endothelial Cell Growth Factor Receptor, Reduces Down-Regulation of Tight Junction Protein, and Significantly Reduces the Degree to which the Blood-Brain Barrier is Pathological Impaired The physiological blood-brain barrier as constructed by Method 2 in the Example 1 was used as a model. Axitinib was added to the Transwell chamber. After the drug was allowed to act for 24 hours, the Transwell cell with bEnd.3 cells grown was transferred to another 12-well plate, washed with PBS for three times, fixed with 4% formaldehyde, and blocked with 10% bovine serum albumin for 30 minutes. Thereafter, Claudin-5 primary antibody was added and incubated at 4° C. overnight, and finally was incubated with fluorescently-labeled secondary antibody for 1 hour. The nucleus was counterstained with DAPI. Expression of tight junction protein of Claudin-5 was observed with a laser confocal microscope. The results were shown in FIG. 8.

Figure 8:
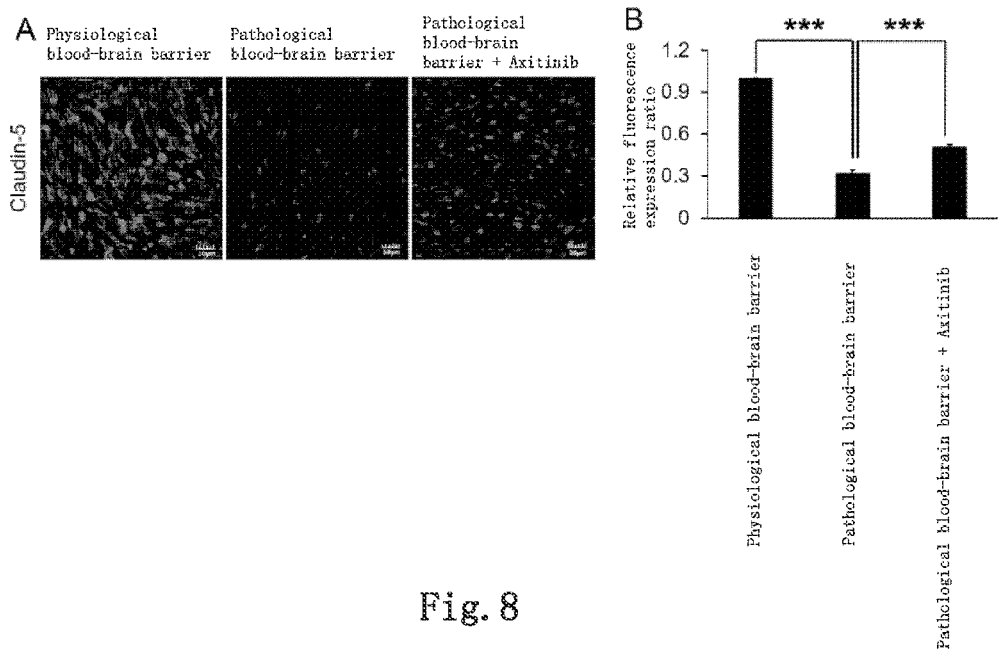
FIG. 8: Degree to which tight junction protein Claudin-5 by Axitinib in vitro, and degree to which a pathological blood-brain barrier is impaired. A transwell model of co-incubation of brain microvascular endothelial cells bEnd.3 and glioma cells U87 MG simulates a pathological blood-brain barrier. Axitinib was allowed to act on the Transwell chamber. After 24 hours, immunofluorescent staining was performed on bEnd.3 cells on the Transwell chamber membrane. A physiological blood-brain barrier simulated by a Transwell model of brain microvascular endothelial cell bEnd.3 was used as a positive control group. Panel A shows the the expression results of tight junction protein Claudin-5 as observed by a confocal microscope. Panel B is the result of fluorescence semi-quantitative analysis of Claudin-5 expression by Image J (n=3).

As can be seen from the results shown in FIG. 8, Axitinib can block the binding of vascular endothelial cell growth factor (VEG F) and vascular endothelial cell growth factor receptor (VEGFR), reduce down-regulation of expression of the blood-brain barrier tight junction protein of Claudin-5, and significantly reduce the degree to which the blood-brain barrier is pathologically impaired.

The physiological blood-brain barrier as constructed by Method 2 in the Example 1 was used as a model. Axitinib at different concentrations was added to the Transwell chamber for stimulation. After 24 hours, cell transmembrane resistance value was measured, and the results were shown in FIG. 9

Figure 9:
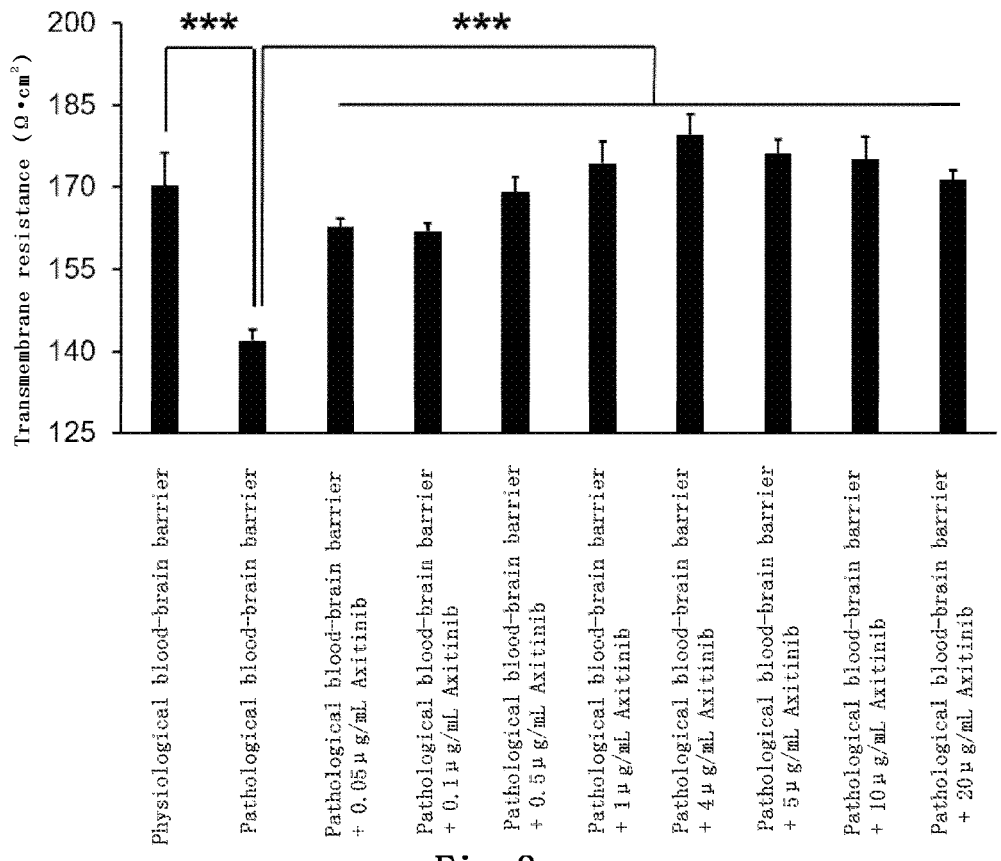
FIG. 9: Dose-dependent promotion of function recovery of a pathological blood-brain barrier to a state close to a physiological barrier by Axitinib in vitro. A Transwell model of co-incubation of brain microvascular endothelial cells bEnd.3 and glioma cells U87 MG simulates a pathological blood-brain barrier. Axitinib at different concentrations (0, 0.05 μg/mL, 0.1 μg/mL, 0.5 g/mL, 1 μg/mL, 4 μg/mL, 5 μg/mL, 10 μg/mL, 20 μg/mL) was allowed to act on the Transwell chamber. After 24 hours, cell transmembrane resistances were detected by a cell resistance meter. A physiological blood-brain barrier simulated by a Transwell model of brain microvascular endothelial cell bEnd.3 was used as a positive control (n=5).

As can be seen the results shown in FIG. 9, the effect of Axitinib in regulating blood-brain barrier function to recovery from a pathologically impaired state to a state close to a physiological barrier is dose-dependent. Axitinib can effectively reduce blood-brain barrier permeability, and promote recovery of a blood-brain barrier function from a pathologically impaired state to a state close to a physiological barrier when Axitinib is at a concentration of 0.5~20 µg/mL (1.29-51.75 µM).

Example 4 Axitinib and Analogs Thereof Inhibit the Vascular Endothelial Cell Growth Factor-Phosphatidylinositol Kinase-Protein Kinase B (VEGF-PI3K-AKT) Signaling Pathway, Reduce the Degree to which Pathological Blood-Brain Barrier Tight Junction Protein is Down-Regulated and Reduce Blood-Brain Barrier Permeability The physiological blood-brain barrier and the pathological blood-brain barrier as constructed in Method 1 and Method 2 in the Example 1 were used as models, respectively. Axitinib (10 µM), an Axitinib analog of phosphatidylinositol kinase (PI3K) inhibitor LY294002 (10 µM), protein kinase B (AKT) agonist SC79 (10 µM) were added into the Transwell chamber of the pathological blood-brain barrier model as constructed in Method 2 in the Example 1. After 24 hours, the Transwell chamber with bEnd.3 cells grown was transferred to another 12-well plate, washed with PBS for 3 times, and 0.5 mL HBSS nutrient solution was added to the chamber, and the outer chamber was supplemented with 1.5 mL HBSS nutrient solution. The cells were equilibrated at 37° C. for 15 minutes. Cell transmembrane resistance was detected by a cell resistance meter. The results are shown in FIG. 10.

The physiological blood-brain barrier and the pathological blood-brain barrier as constructed in Method 1 and Method 2 in the Example 1 were used as models, respectively. Axitinib (10 µM), an Axitinib analog of phosphatidylinositol kinase (PI3K) inhibitor LY294002 (10 µM), protein kinase B (AKT) agonist SC79 (10 µM) were added into the Transwell chamber of the pathological blood-brain barrier model as constructed in Method 2 in the Example 1. After 24 hours, the Transwell chamber with bEnd.3 cells was transferred to another 12-well plate, washed with PBS for 3 times. A solution of dextran having a molecular weight of 10 kDa, which is fluorescently-labeled by a FITC-label, in HBSS was added to the chamber, and the outer chamber was supplemented with 1.5 mL HBSS nutrient solution. After the cells were incubated at 37° C. in the dark for 4 hours, concentration of FITC-dextran transferred to the outer chamber via the Transwell chamber was detected with a fluorescence spectrophotometer. The results were shown in FIG. 11.

The physiological blood-brain barrier and the pathological blood-brain barrier as constructed in Method 1 and Method 2 in the Example 1 were used as models, respectively. Axitinib (10 µM), an Axitinib analog of phosphatidylinositol kinase (PI3K) inhibitor LY294002 (10 µM), protein kinase B (AKT) agonist SC79 (10 µM) were added into the Transwell chamber of the pathological blood-brain barrier model as constructed in Method 2 in Example 1. After 24 hours, the Transwell chamber with bEnd.3 cells grown was taken out, and washed with PBS for 3 times, then fixed with 4% formaldehyde, and blocked with 10% bovine serum albumin for 30 minutes. Thereafter, Claudin-5/Occludin primary antibody was added, and was incubated at 4° C. overnight, and finally was incubated with fluorescently-labeled secondary antibody for 1 hour. The nucleus was counterstained with DAPI. Expression of tight junction protein of Claudin-5/Occludin was observed with a laser confocal microscope. The Results were shown in FIG. 12.

Figure 10:
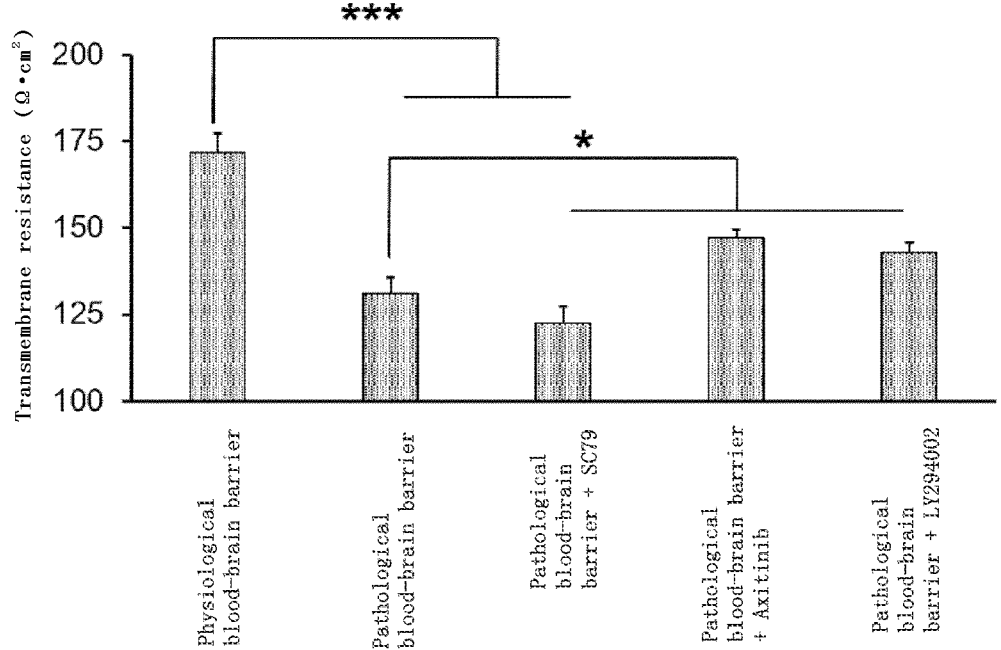
FIG. 10: Co-incubation of U87 MG glioma cells and bEnd.3 cells in vitro, regulation of blood-brain barrier permeability by Axitinib and an analog thereof, and determination of the cell transmembrane resistance. A Transwell model of co-incubation of brain microvascular endothelial cells bEnd.3 and glioma cells U87 MG simulates a pathological blood-brain barrier. Axitinib (10 μM), an Axitinib analog of phosphatidylinositol kinase (PI3K) inhibitor LY294002 (10 μM), protein kinase B (AKT) agonist SC79 (10 μM) were added into the Transwell chamber. After 24 hours, cell transmembrane resistance was detected by a cell resistance meter. A physiological blood-brain barrier simulated by a Transwell model of brain microvascular endothelial cell bEnd.3 was used as a positive control (n=5).
Figure 11:
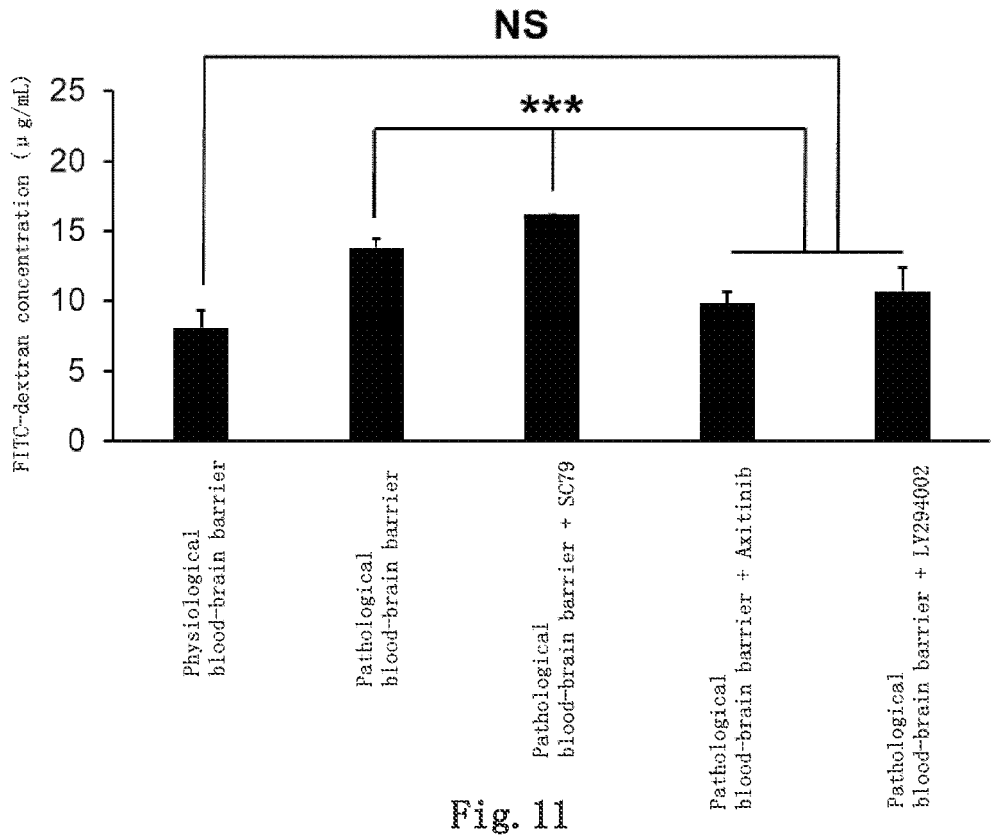
FIG. 11: Co-incubation of U87 MG glioma cells and bEnd.3 cells in vitro, and FITC-dextran transmembrane transport efficiency. A Transwell model of co-incubation of brain microvascular endothelial cells bEnd.3 and glioma cells U87 MG simulates a pathological blood-brain barrier. Axitinib (10 μM), an Axitinib analog of phosphatidylinositol kinase (PI3K) inhibitor LY294002 (10 μM), protein kinase B (AKT) agonist SC79 (10 μM) were added into the Transwell chamber. After 24 hours, the Transwell chamber and the outer chamber were cleaned with PBS, and a solution of FITC-dextran in HBSS was added to the Transwell chamber, and was left for 4 hours. The result as shown in the figure was the concentration of FITC-dextran of the Transwell outer chamber as detected by the fluorescence spectrophotometer. A physiological blood-brain barrier simulated by a Transwell model of brain microvascular endothelial cell bEnd.3 was used as a positive control (n=3).
Figure 12:
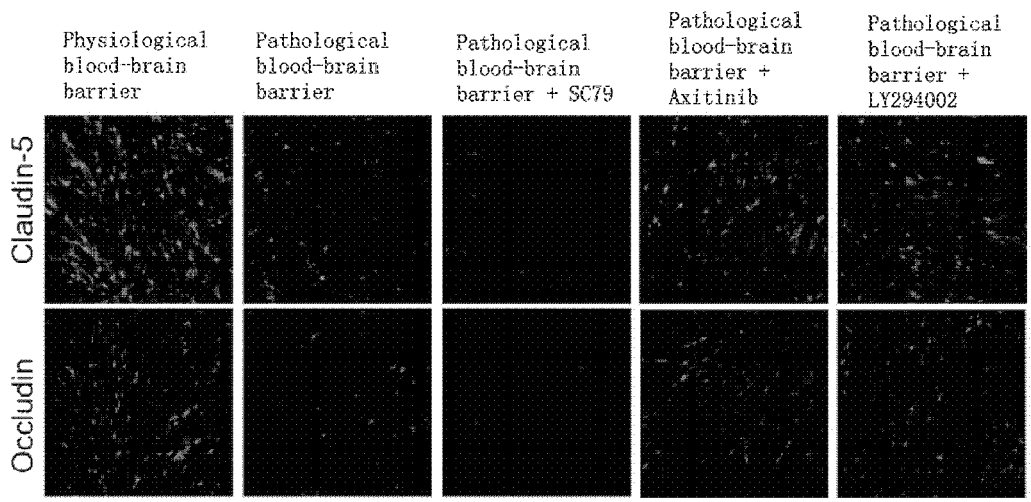
FIG. 12: Co-incubation of U87 MG glioma cells and bEnd.3 cells in vitro, and immunofluorescent staining of blood-brain barrier tight junction protein of Claudin-5/Occludin. A Transwell model of co-incubation of brain microvascular endothelial cells bEnd.3 and glioma cells U87 MG simulates a pathological blood-brain barrier. Axitinib (10 μM), an Axitinib analog of phosphatidylinositol kinase (PI3K) inhibitor LY294002 (10 μM), protein kinase B (AKT) agonist SC79 (10 μM) were added into the Transwell chamber. After 24 hours, immunofluorescent stain was performed on bEnd.3 cells on the Transwell chamber membrane. A physiological blood-brain barrier simulated by a Transwell model of brain microvascular endothelial cell bEnd.3 was used as a positive control. The figure shows the result of tight junction protein Claudin-5/Occludin expression as observed by a confocal microscope.

As can be seen from the results shown in FIGS. 10, 11 and 12, Axitinib acts on vascular endothelial growth factor receptor (VEGFR), and can block the binding of vascular endothelial cell growth factor (VEGF) and vascular endothelial cell growth factor receptor (VEGFR), inhibit vascular endothelial growth factor-phosphatidylinositol kinase-protein kinase B (VEGF-PI3K-AKT) signaling pathway, reduce the degree to which pathological blood-brain barrier tight junction protein of Claudin-5/Occludin is down-regulated, reduce blood-brain barrier permeability, and promote recovery of a blood-brain barrier function from a pathologically impaired state to a state close to a physiological barrier.

In addition, as can be seen from the results shown in FIGS. 10, 11 and 12, an Axitinib analog of phosphatidylinositol kinase (PI3K) inhibitor LY294002 acts on phosphatidylinositol kinase (PI3K) sites, and can inhibit the vascular endothelial cell growth factor-phosphatidylinositol kinase-protein kinase B (VEGF-PI3K-AKT) signaling pathway, reduce the degree to which pathological blood-brain barrier tight junction protein of Claudin-5/Occludin is down-regulated, reduce blood-brain barrier permeability, and promote recovery of a blood-brain barrier function from a pathologically impaired state to a state close to a physiological barrier.

Example 5 Axitinib and Analogs Thereof Regulate the Decrease in Pathological Blood-Brain Barrier Permeability and do not Produce Anti-Glioma Effects at Therapeutic Concentrations The physiological blood-brain barrier and the pathological blood-brain barrier as constructed in Method 1 and Method 2 in the Example 1 were used as models, respectively. Axitinib (10 µM) and an Axitinib analog of phosphatidylinositol kinase (PI3K) inhibitor LY294002 (10 µM) were added into the Transwell chamber of the pathological blood-brain barrier model as constructed in Method 2 in the Example 1. After 24 hours, the Transwell chamber with bEnd.3 cells grown was transferred to another 12-well plate. 50 µL of 5 mg/mL thiazole blue was added. In addition, 150 µL of 5 mg/mL thiazole blue was added to the Transwell outer chamber with U87 MG cells grown, and was further incubated for 4 hours. The culture medium was removed. The purple formazan in each of the wells was dissolved in 2000 µL of dimethyl sulfoxide, which was placed in a thermostat shaking box for 15 minutes, and transferred to a 96-well plate at 200 µL/well. Absorbance at 570 nm was measured with a microplate reader. The survival rate of cells was calculated according to the following formula:

Survival rate of cells (%)=(absorbance value of a test group/absorbance value of a control group)×100%

Figure 13:
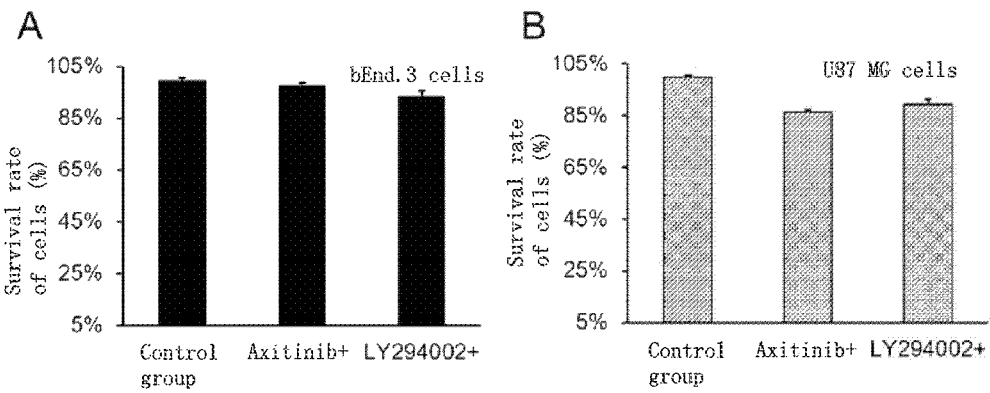
FIG. 13: Evaluation of cell survival rate in a Transwell model. A Transwell model of co-incubation of brain microvascular endothelial cells bEnd.3 and glioma cells U87 MG simulates a pathological blood-brain barrier. Axitinib (10 μM) and an Axitinib analog of phosphatidylinositol kinase (PI3K) inhibitor LY294002 (10 μM) were added into the Transwell chamber. After 24 hours, the survival rate of bEnd.3 cells in the Transwell chamber (Panel A) and U87 MG cells in the Transwell outer chamber (Panel B) were detected by tetrazolium blue colorimetry (n=3).

The results of survival rate of bEnd.3 cells and U87 MG cells were shown in FIG. 13.

In addition, bEnd.3 cells and U87 MG glioma cells were used as model cells to evaluate the cytotoxicity of Axitinib and an Axitinib analog of phosphatidylinositol kinase (PI3K) inhibitor LY294002 with the tetrazolium blue colorimetric method. 200 µL suspensions of well-grown bEnd.3 cells and U87 MG glioma cells were inoculated into a 96-well plate at a density of 1×10⁴/well, and were incubated at 37° C. and 5% $CO_2$ until the cells adhere. Then, Axitinib at different concentrations (0~10 µg/mL) and an Axitinib analog of phosphatidylinositol kinase (PI3K) inhibitor LY294002 were added. An untreated group was used as a blank control. Each of the group was repeated 3 times. After a further incubation of 48 hours, 20 µL of 5 mg/mL thiazole blue was added to each of the wells, and was further incubate for 4 hours. The culture medium was removed. 200 µL of dimethyl sulfoxide was added to each of the wells. The 96-well plate was placed in a thermostat shaking box for 15 minutes. Absorbance at 570 nm was measured with a microplate reader. The results of survival rate of bEnd.3 cells and U87 MG cells were shown in FIG. 14.

Figure 15:
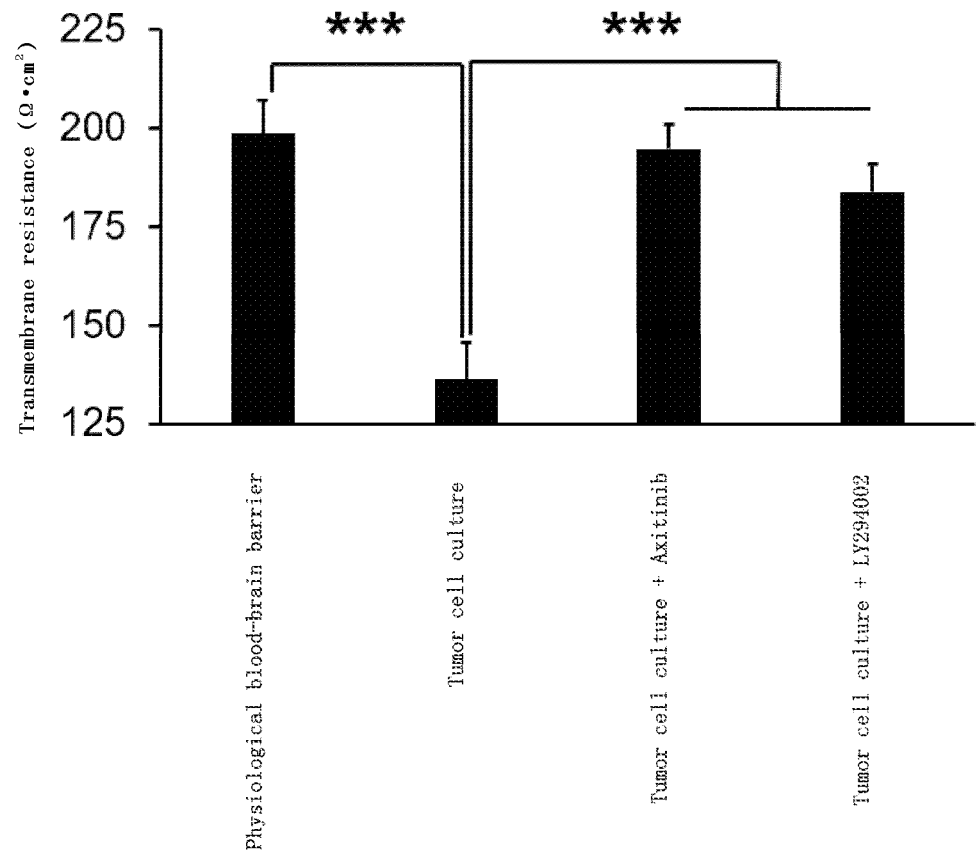
FIG. 15: Co-incubation of a tumor cell culture and bEnd.3 cells in vitro, regulation of blood-brain barrier permeability by Axitinib and an analog thereof, and determination of a cell transmembrane resistance. A Transwell model of co-incubation of brain microvascular endothelial cells bEnd.3 and glioma cells U87 MG simulates a pathological blood-brain barrier. Once a pathological blood-brain barrier model was formed, U87MG glioma cells in the outer chamber of Transwell were removed, while the tumor cell cultures were remained. Axitinib (10 μM) and an Axitinib analog of phosphatidylinositol kinase (PI3K) inhibitor LY294002 (10 μM) were added to the Transwell chamber. After 24 hours, cell transmembrane resistance was detected by a cell resistance meter. A physiological blood-brain barrier simulated by a Transwell model of brain microvascular endothelial cell bEnd.3 was used as a positive control (n=5).

The physiological blood-brain barrier and the pathological blood-brain barrier as constructed in Method 1 and Method 2 in the Example 1 were used as models, respectively. Once a pathological blood-brain barrier model was formed, U87MG glioma cells in the outer chamber of Transwell were removed, while the tumor cell cultures were remained. Axitinib (10 µM) and an Axitinib analog of phosphatidylinositol kinase (PI3K) inhibitor LY294002 (10 µM) were added to the Transwell chamber. After 24 hours, the Transwell chamber with bEnd.3 cells grown was transferred to another 12-well plate, and washed with PBS for 3 times. 0.5 mL of HBSS nutrient solution was added to the chamber, and the outer chamber was supplemented with 1.5 mL HBSS nutrient solution. The cells were equilibrated at 37° C. for 15 minutes. Cell transmembrane resistance was detected by a cell resistance meter. The results were shown in FIG. 15.

Figure 16:
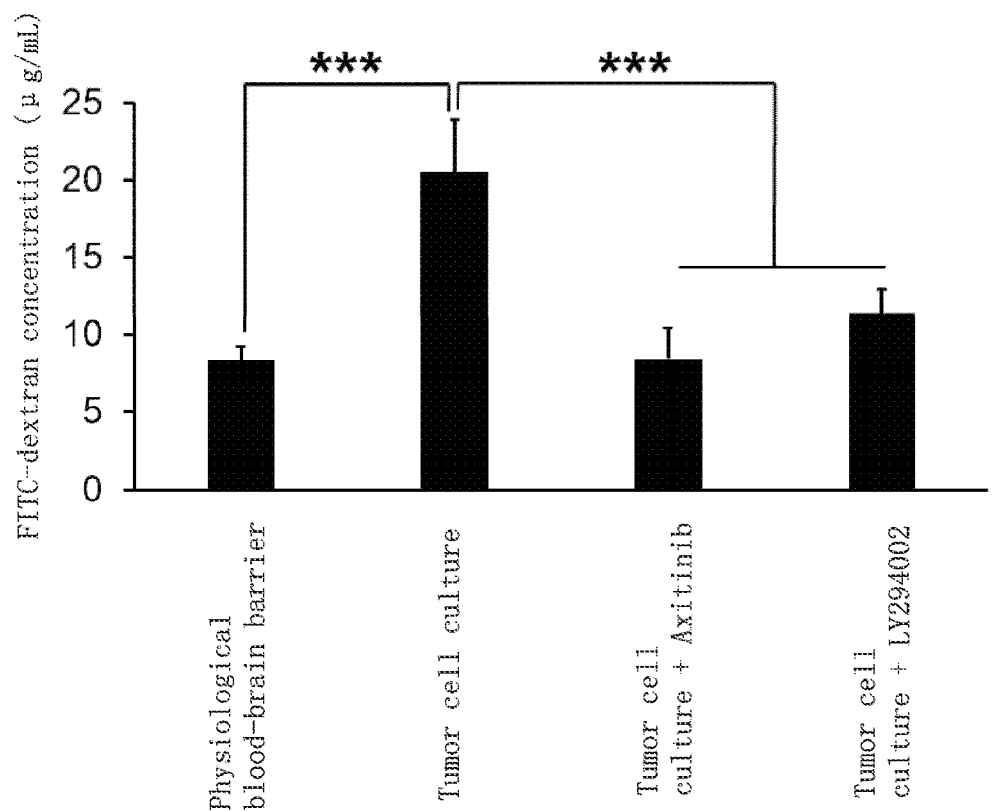
FIG. 16: Co-incubation of a tumor cell culture and bEnd.3 cells in vitro, and FITC-dextran transmembrane transport efficiency. A Transwell model of co-incubation of brain microvascular endothelial cells bEnd.3 and glioma cells U87 MG simulates a pathological blood-brain barrier. Once a pathological blood-brain barrier model was formed, U87MG glioma cells in the outer chamber of Transwell were removed, while the tumor cell cultures were remained. Axitinib (10 μM) and an Axitinib analog of phosphatidylinositol kinase (PI3K) inhibitor LY294002 (10 μM) were added to the Transwell chamber. After 24 hours, the Transwell chamber and the outer chamber were cleaned with PBS, and a FITC-dextran solution in HBSS was added to the Transwell chamber, and was allowed to act for 4 hours. The result as shown in the figure was the FITC-dextran concentration of the Transwell outer chamber as detected by a fluorescence spectrophotometer. A physiological blood-brain barrier simulated by a Transwell model of brain microvascular endothelial cell bEnd.3 was used as a positive control (n=3).

The physiological blood-brain barrier and the pathological blood-brain barrier as constructed in Method 1 and Method 2 in the Example 1 were used as models, respectively. Once a pathological blood-brain barrier model was formed, U87MG glioma cells in the outer chamber of Transwell were removed, while the tumor cell cultures were remained. Axitinib (10 µM) and an Axitinib analog of phosphatidylinositol kinase (PI3K) inhibitor LY294002 (10 µM) were added to the Transwell chamber. After 24 hours, the Transwell chamber with bEnd.3 cells grown was transferred to another 12-well plate, and washed with PBS for 3 times. A solution of dextran having a molecular weight of 10 kDa, which is fluorescently-labeled by a FITC-label, in HBSS was added to the chamber, and the outer chamber was supplemented with 1.5 mL HBSS nutrient solution. After the cells were incubated at 37° C. in the dark for 4 hours, concentration of FITC-dextran transferred to the outer chamber via the Transwell chamber was detected with a fluorescence spectrophotometer. The results were shown in FIG. 16.

Figure 17:
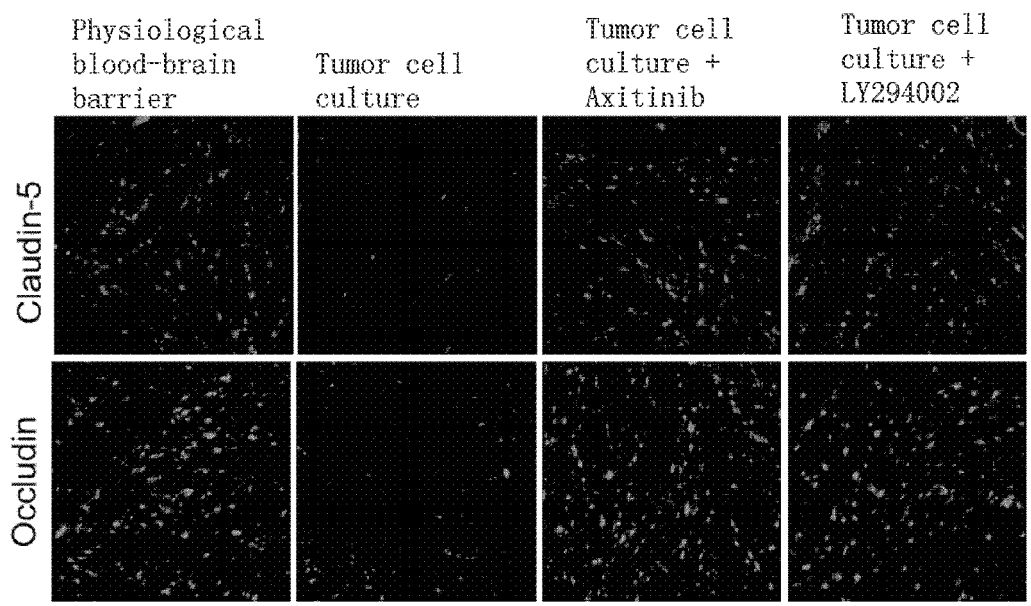
FIG. 17: Co-incubation of a tumor cell culture and bEnd.3 cells in vitro, and immunofluorescent staining of a blood-brain barrier tight junction protein of Claudin-5/Occludin. A Transwell model of co-incubation of brain microvascular endothelial cells bEnd.3 and glioma cells U87 MG simulates a pathological blood-brain barrier. Once a pathological blood-brain barrier model was formed, U87MG glioma cells in the outer chamber of Transwell were removed, while the tumor cell cultures were remained. Axitinib (10 μM) and an Axitinib analog of phosphatidylinositol kinase (PI3K) inhibitor LY294002 (10 μM) were added to the Transwell chamber. After 24 hours, immunofluorescent staining was performed on bEnd.3 cells on the Transwell chamber membrane. A physiological blood-brain barrier simulated by a Transwell model of brain microvascular endothelial cell bEnd.3 was used as a positive control. The figure shows the result of tight junction protein Claudin-5/Occludin expression as observed by a confocal microscope.

The physiological blood-brain barrier and the pathological blood-brain barrier as constructed in Method 1 and Method 2 in the Example 1 were used as models, respectively. Once a pathological blood-brain barrier model was formed, U87MG glioma cells in the outer chamber of Transwell were removed, while the tumor cell cultures were remained. Axitinib (10 µM) and an Axitinib analog of phosphatidylinositol kinase (PI3K) inhibitor LY294002 (10 µM) were added to the Transwell chamber. After 24 hours, the Transwell chamber with bEnd.3 cells grown was taken out, and washed with PBS for 3 times, then fixed with 4% formaldehyde, and blocked with 10% bovine serum albumin for 30 minutes. Thereafter, Claudin-5/Occludin primary antibody was added, and was incubated at 4° C. overnight, and finally was incubated with fluorescently-labeled secondary antibody for 1 hour. The nucleus was counterstained with DAPI. Expression of tight junction protein of Claudin-5/Occludin was observed with a laser confocal microscope. The Results were shown in FIG. 17.

Figure 14:
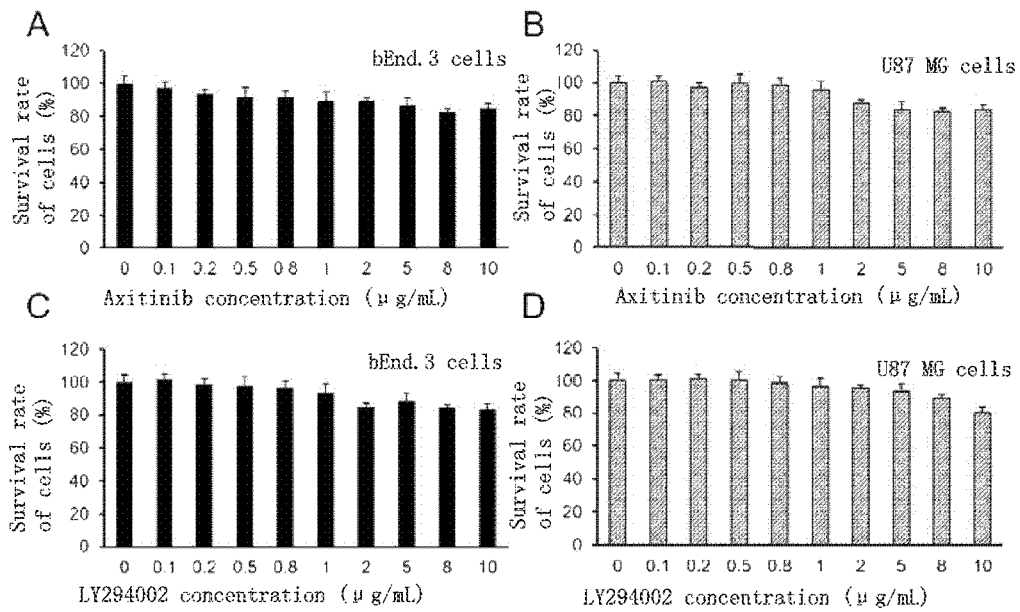
FIG. 14: Evaluation of Cytotoxicity for Axitinib and an analog thereof. 200 μL suspensions of well-grown bEnd.3 cells and U87 MG glioma cells were inoculated into a 96-well plate at a density of $1\times10^4$/well. After adherent growth of the cells, Axitinib at different concentrations (0~10 μg/mL) and an Axitinib analog of phosphatidylinositol kinase (PI3K) inhibitor LY294002 were added. An untreated group was used as a blank control. Cell survival rate was detected by tetrazolium blue colorimetry. Panel A and panel B are cytotoxicity of Axitinib on bEnd.3 cells and U87 MG glioma cells, respectively, and panel C and panel D are cytotoxicity of Axitinib analog of phosphatidylinositol kinase (PI3K) inhibitor LY294002 on bEnd.3 cells and U87 MG glioma cells, respectively (n=3).

As can be seen from the results shown in FIGS. 13 and 14, Axitinib (10 µM) and an Axitinib analog of phosphatidylinositol kinase (PI3K) inhibitor LY294002 (10 µM) do not produce significant cytotoxicity on bEnd.3 cells and U87MG cells at a therapeutic dose. All of survival rate of the cells were greater than 80%. In addition, ss can be seen from the results shown in FIGS. 15, 16 and 17, under a pathological condition of maintaining blood-brain barrier function impaired, after the action of Axitinib and analogs thereof, the degree to which pathological blood-brain barrier tight junction protein of Claudin-5/Occludin is down-regulated is reduced, blood-brain barrier permeability is reduced, and the blood-brain barrier function is recovered from a pathologically impaired state to a state close to a physiological barrier. The above results indicate that Axitinib and analogs thereof only play a role in regulating pathological blood-brain barrier permeability at a therapeutic dose, and have no antitumor effect on U87 MG glioma cells.

Example 6 Axitinib Promotes Recovery of a Blood-Brain Barrier Function from a Pathologically Impaired State to a State Close to a Physiological Barrier in Glioma Model Animals Male BABL/c nude mice (20±2 g) were used as the model animals. U87-luci glioma cells expressing luciferase were inoculated in the striatum area of nude mice at a concentration of 5×10⁵ cells/5 µL by means of a brain stereotaxic instrument (inoculation coordinates, 0.8 mm on the anterior side of bregma, 2 mm on the right side, and 3 mm in depth), to construct an in situ glioma model. Axitinib diluted with 0.2% injection grade Tween 80 solution was injected into tail veins at an administration dose of 10 mg/kg. After 24 hours, an Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The Results were shown in FIG. 18. The Evans blue was extracted from the brain tissue with an organic solvent of N,N-dimethylformamide. The amount of Evans blue permeated into the brain was quantitatively detected by ultraviolet spectrophotometry. The results were shown in FIG. 19.

Figure 18:
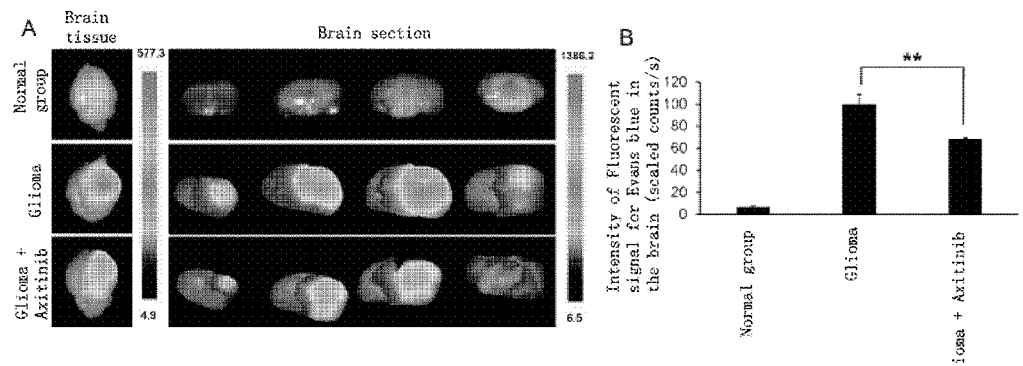
FIG. 18: Regulation of decrease in pathological blood-brain barrier permeability by Axitinib in a glioma model. Axitinib was injected into tumor-bearing animals into tail veins at an administration dose of 10 mg/kg. After 24 hours, an Evans blue solution was injected into tail veins at an administration dose of 5 mg/kg. After 4 hours, the intact brain of the nude mice was taken by cardiac perfusion. Panel A is the result of the distribution intensity of Evans blue in brain tissues as qualitatively observed with a small animal live imaging instrument, and Panel B shows the semi-quantitative results of the fluorescence signal of Evans blue (n=3).
Figure 19:
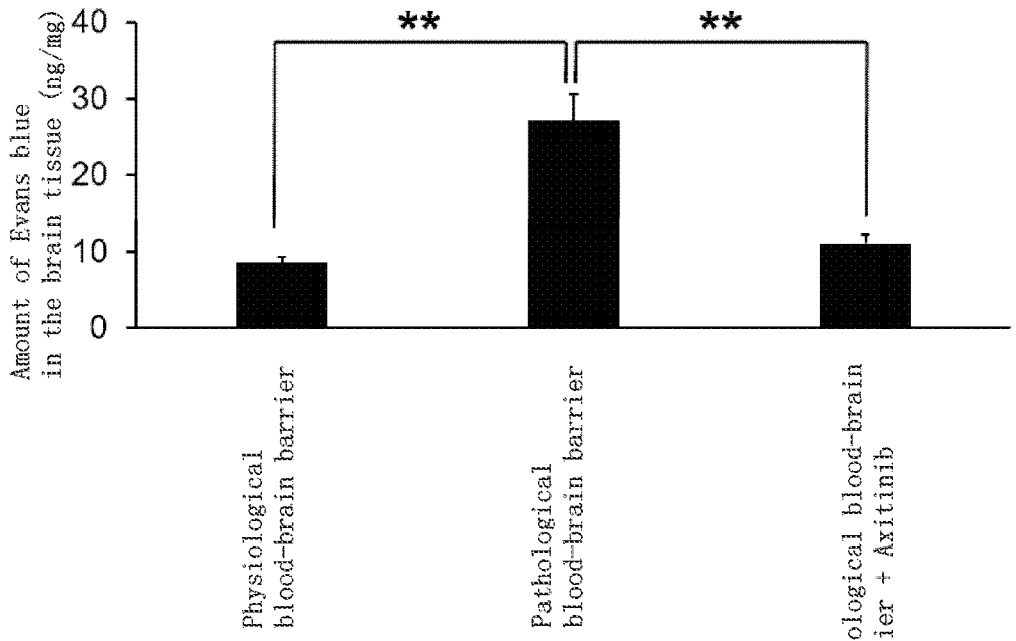
FIG. 19: Regulation of decrease in pathological blood-brain barrier permeability and reduction of the amount of Evans blue permeated into the brain by Axitinib in a glioma model. Axitinib was injected into tumor-bearing animals into tail veins at an administration dose of 10 mg/kg. After 24 hours, an Evans blue solution was injected into tail veins at an administration dose of 5 mg/kg. After 4 hours, the intact brain of the nude mice was taken by cardiac perfusion. The Evans blue was extracted from the brain tissue with an organic solvent of N,N-dimethylformamide. The result as shown in the figure is the amount of Evans blue permeated into the brain as quantitatively detected by ultraviolet spectrophotometry (n=3).

As can be seen from the results shown in FIGS. 18 and 19, as compared with the tumor-bearing control group, after the treatment of Axitinib, the amount of Evans blue permeated into the brain is reduced, which shows that the blood-brain barrier permeability is significantly reduced. It indicates that Axitinib can reduce blood-brain barrier permeability and promote recovery of a blood-brain barrier function from a pathologically impaired state to a state close to a physiological barrier.

Figure 20:
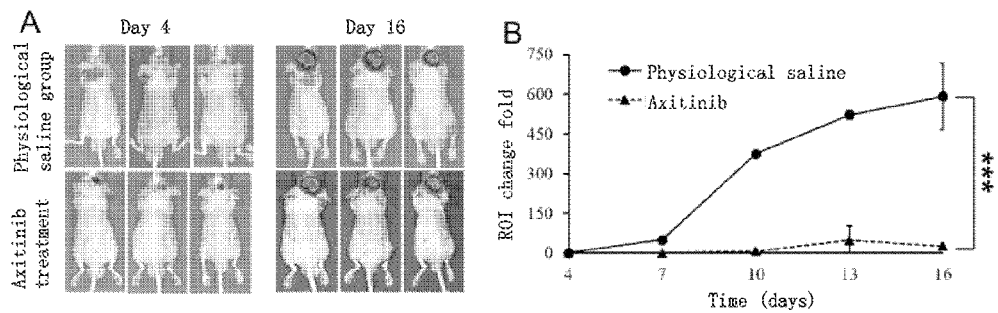
FIG. 20: Regulation of decrease in pathological blood-brain barrier permeability and treatment of glioma by Axitinib. On Day 4 of tumor bearing, administration was started by injecting Axitinib diluted with 0.2% of Tween 80 solution (injection grade) into tumor-bearing animals into tail veins at a dose of 10 mg/kg. Administration was performed for 7 consecutive days. Growth of glioma was monitored by a bioluminescent imaging technology. Panel A qualitatively indicates the size of the brain tumor on Day 4 and Day 16 of tumor bearing. Panel B is a real-time (Day 4, 7, 10, 13, 16) quantitative monitoring curve for growth of glioma (n=5). A physiological saline group was used as control.
Figure 21:
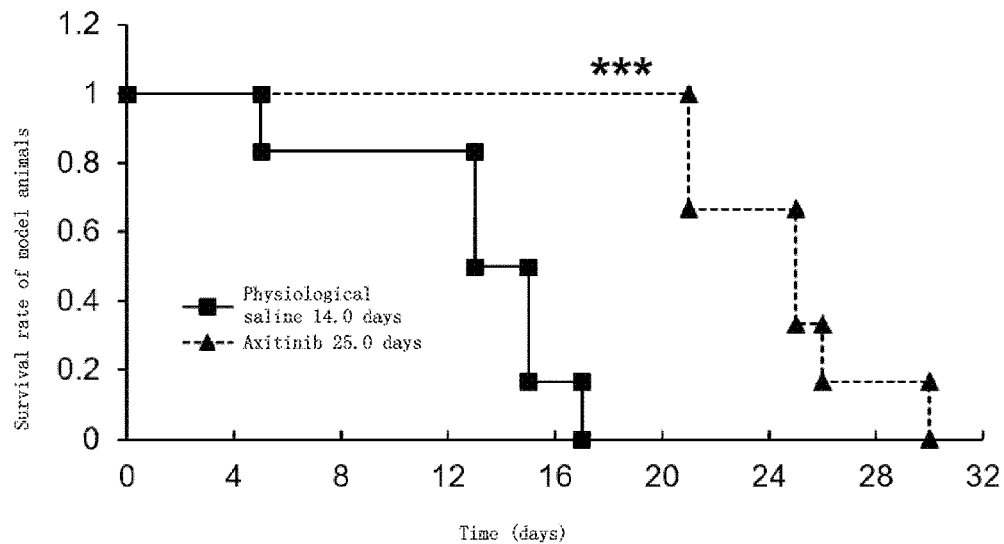
FIG. 21: Survival curve of glioma model animals. After treatment by administration of Axitinib was accomplished, life cycles of animals in the physiological saline group and the Axitinib treatment group were recorded (n=6).

Example 7 Axitinib Regulates Blood-Brain Barrier Permeability and Treats Gliomas in Glioma Model Animals Male BABL/c nude mice (20±2 g) were used as the model animals. U87-luci glioma cells expressing luciferase were inoculated in the striatum area of nude mice at a concentration of 5×10⁵ cells/5 µL by means of a brain stereotaxic instrument (inoculation coordinates, 0.8 mm on the anterior side of bregma, 2 mm on the right side, and 3 mm in depth), to construct an in situ glioma model. On Day 4 of tumor bearing, administration was started by injecting Axitinib diluted with 0.2% of Tween 80 solution (injection grade) into tumor-bearing animals in tail veins at a dose of 10 mg/kg. Administration was performed for 7 consecutive days. Growth of glioma was monitored by a bioluminescent imaging technology. The results are shown in FIG. 20. After Axitinib treatment, the results of life cycles of the glioma model animals were recorded as shown in FIG. 21.

It can be seen from the results shown in FIG. 20, as compared with the saline control group, after the Axitinib treatment, growth of glioma in situ is significantly inhibited. It can be seen from the results shown in FIG. 21, after the Axitinib treatment, life cycle of the animal was significantly prolonged.

Example 8 Parkinson's Disease Causes Pathological Impairment of the Blood-Brain Barrier and an Increase in Permeability Male C57/BL6 (6-8 w) mice were used as the model animals. 1-methyl-4-phenyl-1,2,3,6-tetrahydropyridine dissolved in physiological saline was injected intraperitoneally at an administration dose of 20 mg/kg for 7 consecutive days to construct a model of Parkinson's disease. An Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The results were shown in FIG. 22. The Evans blue was extracted from the brain tissue with an organic solvent of N,N-dimethylformamide. The amount of Evans blue permeated into the brain was quantitatively detected by ultraviolet spectrophotometry. The results were shown in FIG. 23.

Figure 22:
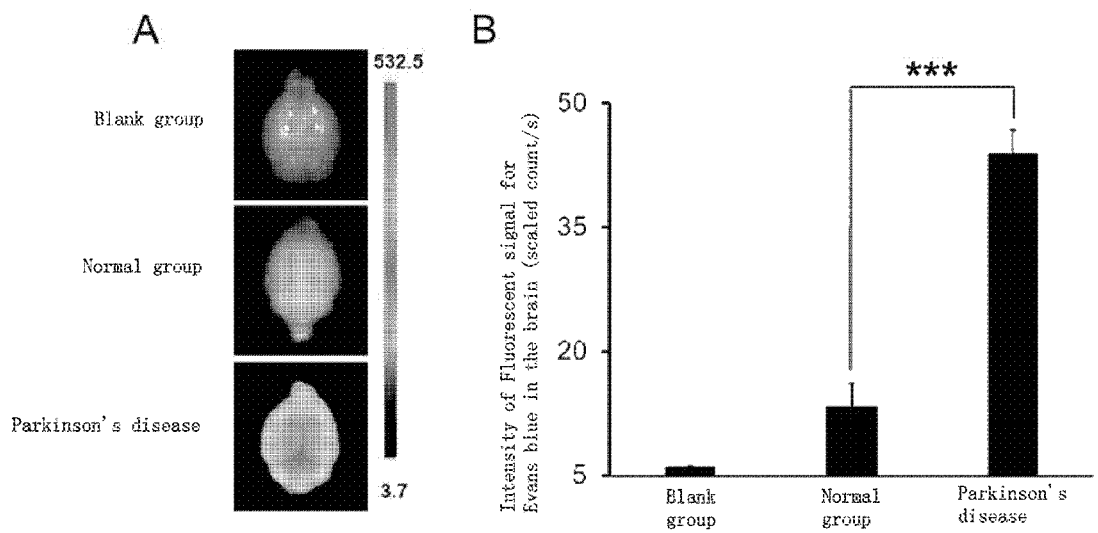
FIG. 22: Pathological impairment of the blood-brain barrier and increase in permeability caused by Parkinson's disease. Male C57/BL6 (6-8 w) mice were used as model animals. A model of Parkinson's disease was established by stimulus of administration of 1-methyl-4-phenyl-1,2,3,6-tetrahydropyridine. An Evans blue solution was injected into tail veins at an administration dose of 5 mg/kg. After 4 hours, the intact brain of the nude mice was taken by cardiac perfusion. Panel A is the result of distribution intensity of Evans blue in brain tissues as qualitatively observed with a small animal live imaging instrument, and Panel B shows the semi-quantitative results of the fluorescent signal of Evans blue (n=3).
Figure 23:
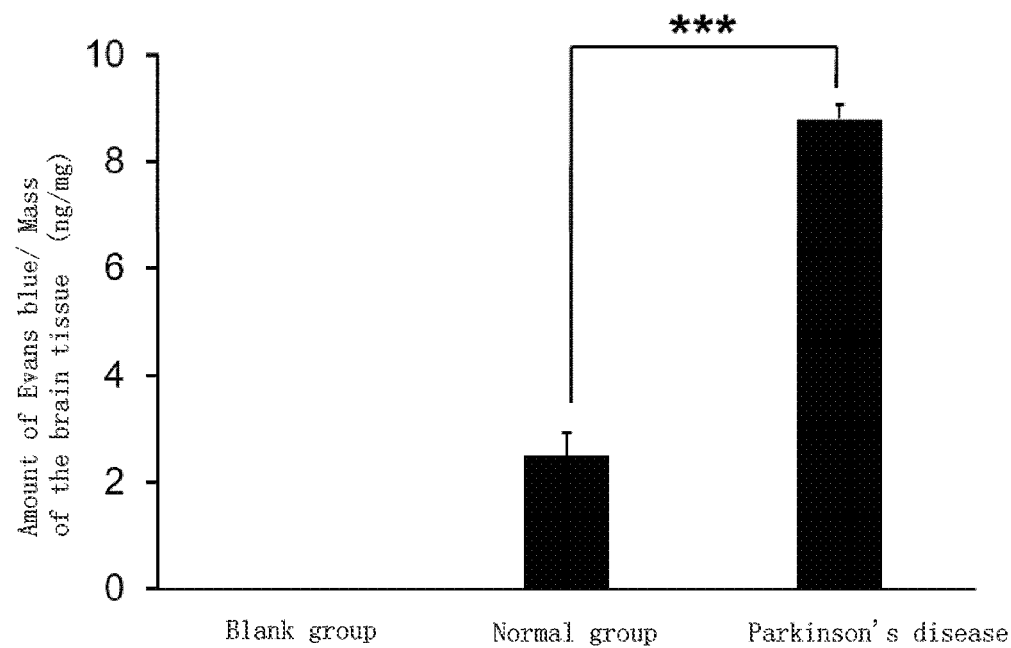
FIG. 23: Occurrence of Parkinson's disease accompanied by an increase in the blood-brain barrier permeability and the amount of Evans blue permeated into the brain. Male C57/BL6 (6-8 w) mice were used as model animals. A model of Parkinson's disease was established by stimulus of administration of 1-methyl-4-phenyl-1,2,3,6-tetrahydropyridine. An Evans blue solution was injected into tail veins at an administration dose of 5 mg/kg. After 4 hours, the intact brain of the nude mice was taken by cardiac perfusion. The Evans blue was extracted from the brain tissue with an organic solvent of N,N-dimethylformamide. The result as shown in the figure is the amount of Evans blue permeated into the brain as quantitatively detected by ultraviolet spectrophotometry (n=3).

As can be seen from the results shown in FIGS. 22 and 23, blood-brain barrier permeability may be significantly increased in Parkinson's disease. As compared with a normal brain tissue, in the model of Parkinson's disease, the amount of Evans blue permeated into the brain is significantly increased.

Example 9 Axitinib Promotes Recovery of a Blood-Brain Barrier Function from a Pathologically Impaired State to a State Close to a Physiological Barrier in Parkinson's Disease Model Animals Male C57/BL6 (6-8 w) mice were used as the model animals. 1-methyl-4-phenyl-1,2,3,6-tetrahydropyridine dissolved in physiological saline was injected intraperitoneally at an administration dose of 20 mg/kg for 7 consecutive days to construct a model of Parkinson's disease. Axitinib diluted with 0.2% injection grade Tween 80 solution was injected at an administration dose of 10 mg/kg into tail veins. After 24 hours, an Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The results were shown in FIG. 24. The Evans blue was extracted from the brain tissue with an organic solvent of N,N-dimethylformamide. The amount of Evans blue permeated into the brain was quantitatively detected by ultraviolet spectrophotometry. The results were shown in FIG. 25.

Figure 24:
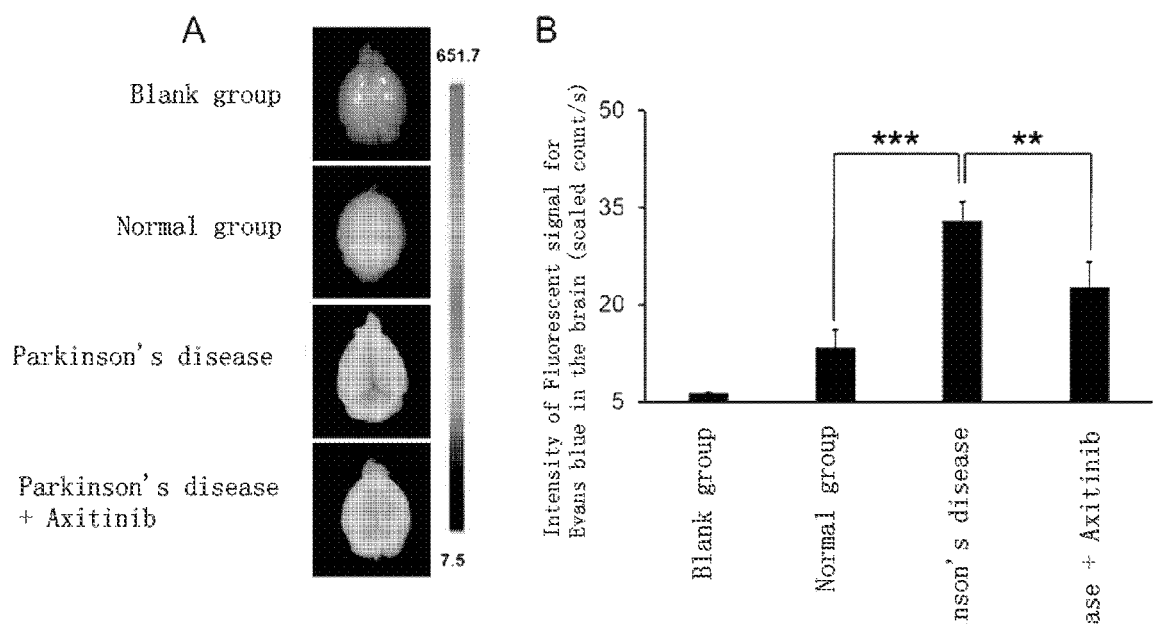
FIG. 24: Regulation of decrease in pathological blood-brain barrier permeability by Axitinib in a model of Parkinson's disease. Male C57/BL6 (6-8 w) mice were used as model animals. A model of Parkinson's disease was established by stimulus of administration of 1-methyl-4-phenyl-1,2,3,6-tetrahydropyridine. Axitinib was injected into model animals of Parkinson's disease in tail veins at an administration dose of 10 mg/kg. After 24 hours, an Evans blue solution was injected into tail veins at an administration dose of 5 mg/kg. After 4 hours, the intact brain of the nude mice was taken by cardiac perfusion. Panel A is the result of distribution intensity of Evans blue in the brain tissue as qualitatively observed with a small animal live imaging instrument, and Panel B shows the semi-quantitative results of the fluorescent signal of Evans blue (n=3).
Figure 25:
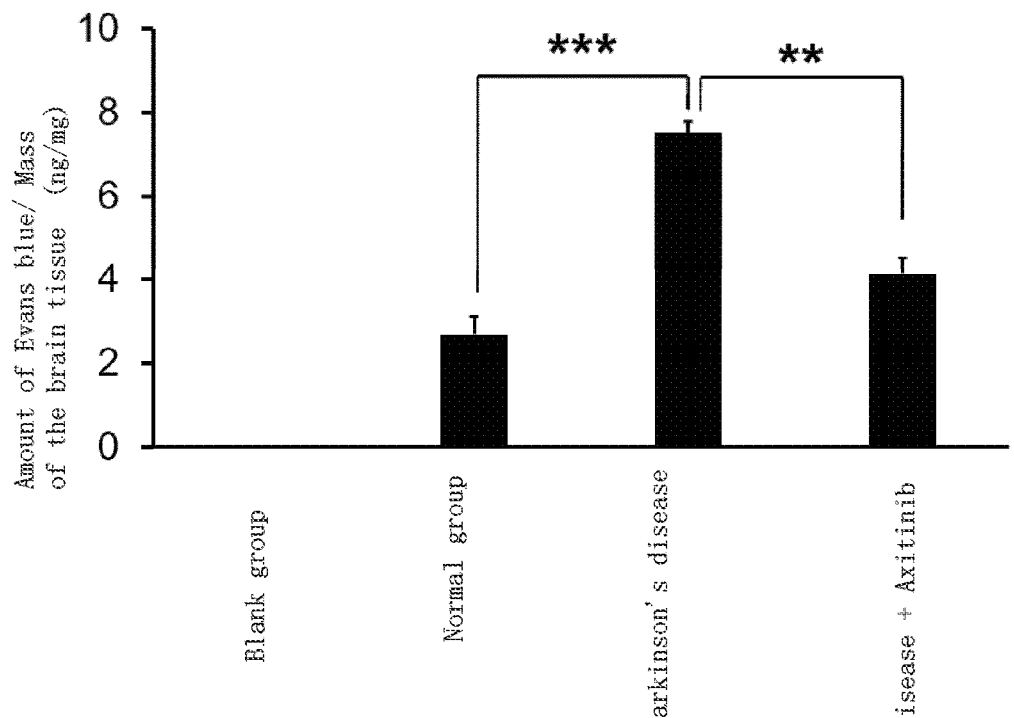
FIG. 25: Regulation of decrease in pathological blood-brain barrier permeability and reduction of the amount of Evans blue permeated into the brain by Axitinib in a model of Parkinson's disease. Axitinib was injected into model animals of Parkinson's disease in tail veins at an administration dose of 10 mg/kg. After 24 hours, an Evans blue solution was injected into tail veins at an administration dose of 5 mg/kg. After 4 hours, the intact brain of the nude mice was taken by cardiac perfusion. The Evans blue was extracted from the brain tissue with an organic solvent of N,N-dimethylformamide. The result as shown in the figure is the amount of Evans blue permeated into the brain as quantitatively detected by ultraviolet spectrophotometry (n=3).

As can be seen from the results shown in FIGS. 24 and 25, as compared with a control group of Parkinson's disease, after the Axitinib treatment, the amount of Evans blue permeated into the brain is reduced, which shows that blood-brain barrier permeability is significantly reduced. It indicates that Axitinib can reduce blood-brain barrier permeability, and promote recovery of a blood-brain barrier function from a pathologically impaired state to a state close to a physiological barrier.

Example 10 Axitinib Regulates Blood-Brain Barrier Permeability and Treats Parkinson's Disease in Parkinson's Disease Model Animals 1. Construction of Parkinson's Disease Model Animal
Male C57/BL6 (6-8 w) mice were used as the model animals. 1-methyl-4-phenyl-1,2,3,6-tetrahydropyridine dissolved in physiological saline was injected intraperitoneally at an administration dose of 20 mg/kg for 7 consecutive days to construct a model of Parkinson's disease.
2. Axitinib Treatment of Parkinson's Disease
2-1 Permeability of Evans Blue in the Brain is Significantly Decreased after the Axitinib Treatment Axitinib diluted with 0.2% injection grade Tween 80 solution was injected into the tumor-bearing animals at an administration dose of 10 mg/kg in tail veins for 7 consecutive days. Levodopa dissolved in normal saline was injected intraperitoneally at an administration dose of 20 mg/kg for 10 consecutive days. After the treatment, an Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The results were shown in FIG. 26. The Evans blue was extracted from the brain tissue with an organic solvent of N,N-dimethylformamide. The amount of Evans blue permeated into the brain was quantitatively detected by ultraviolet spectrophotometry. The results were shown in FIG. 27.

Figure 26:
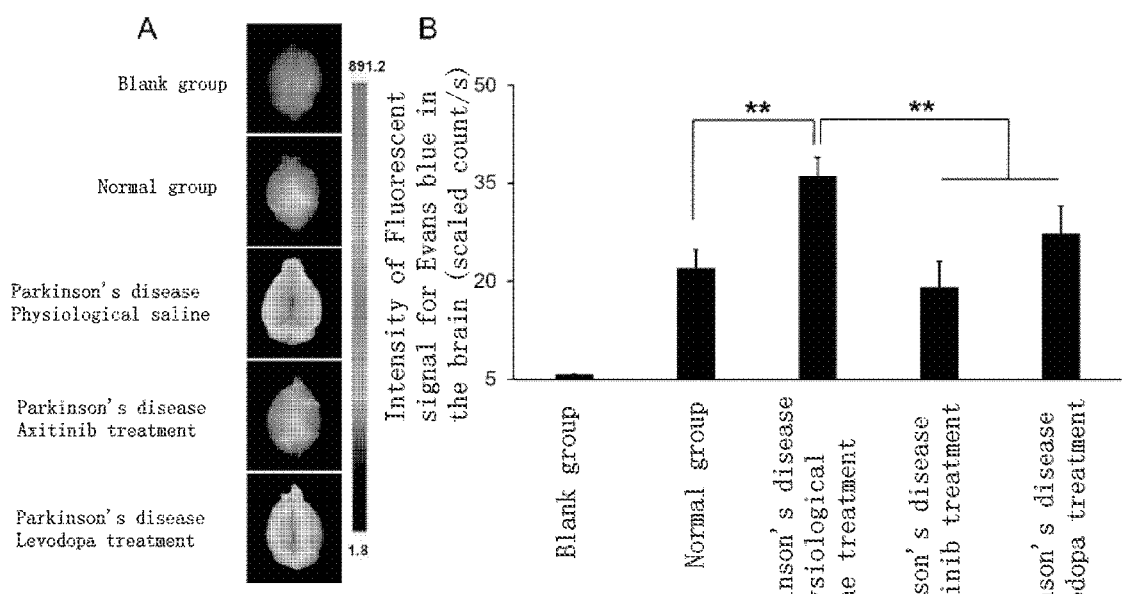
FIG. 26: Regulation of decrease in pathological blood-brain barrier permeability and treatment of Parkinson's disease by Axitinib. Male C57/BL6 (6-8 w) mice were used as model animals. A model of Parkinson's disease was established by stimulus of administration of 1-methyl-4-phenyl-1,2,3,6-tetrahydropyridine. Axitinib was injected into model animals of Parkinson's disease in tail veins at an administration dose of 10 mg/kg for 7 consecutive days. Levodopa dissolved in physiological saline was injected intraperitoneally at an administration dose of 20 mg/kg for 10 consecutive days. After the treatment was accomplished, an Evans blue solution was injected into tail veins at an administration dose of 5 mg/kg. After 4 hours, the intact brain of the nude mice was taken by cardiac perfusion. Panel A is the result of distribution intensity of Evans blue in the brain tissue as qualitatively observed with a small animal live imaging instrument, and Panel B shows the semi-quantitative results of the fluorescent signal of Evans blue (n=3).
Figure 27:
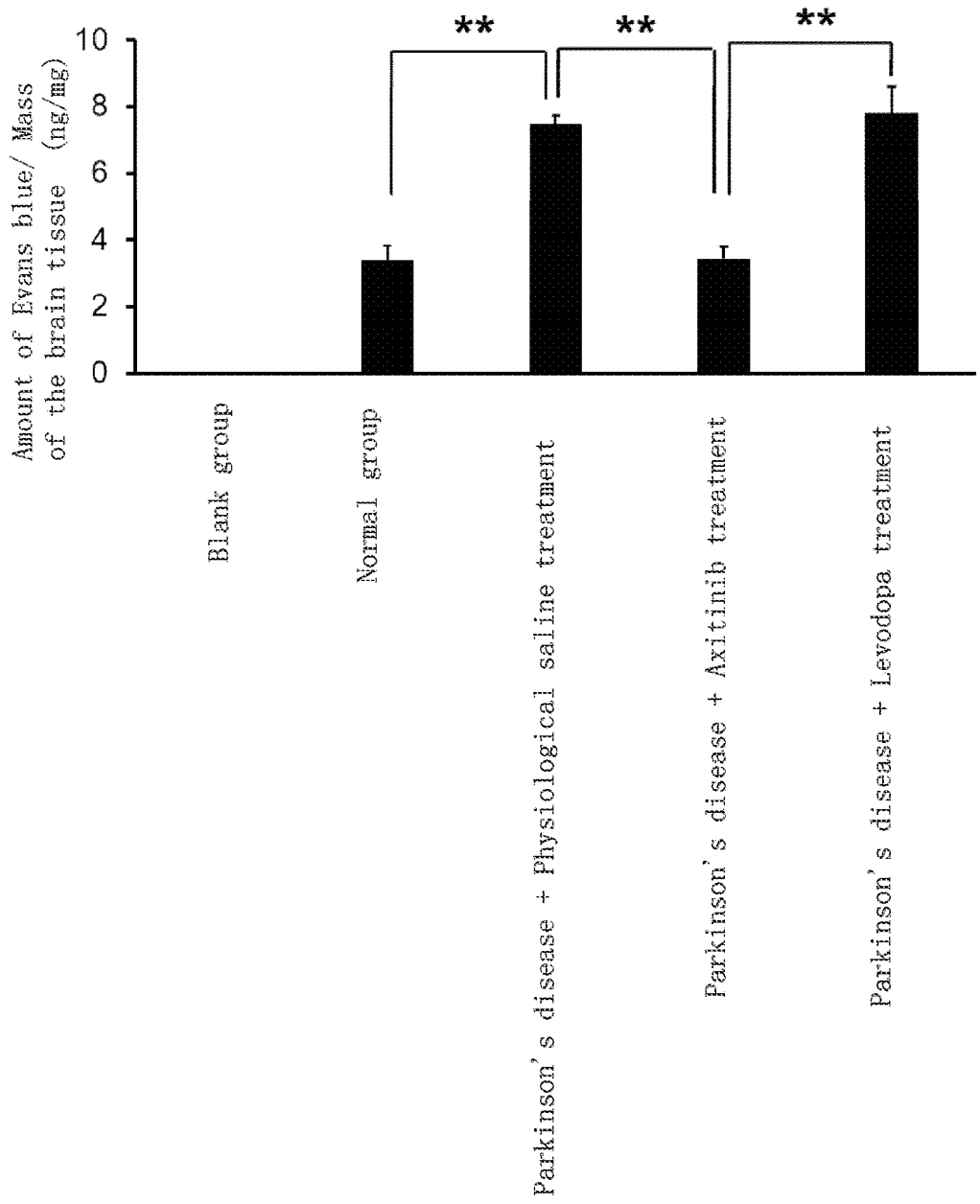
FIG. 27: Regulation of decrease in pathological blood-brain barrier permeability, treatment of Parkinson's disease and reduction of the amount of Evans blue in the brain by Axitinib. Male C57/BL6 (6-8 w) mice were used as model animals. A model of Parkinson's disease was established by stimulus of administration of 1-methyl-4-phenyl-1,2,3,6-tetrahydropyridine. Axitinib was injected into model animals of Parkinson's disease in tail veins at an administration dose of 10 mg/kg for 7 consecutive days. Levodopa dissolved in physiological saline was injected intraperitoneally at an administration dose of 20 mg/kg for 10 consecutive days. After the treatment was accomplished, an Evans blue solution was injected into tail veins at an administration dose of 5 mg/kg. After 4 hours, the intact brain of the nude mice was taken by cardiac perfusion. The Evans blue was extracted from the brain tissue with an organic solvent of N,N-dimethylformamide. The result as shown in the figure is the amount of Evans blue permeated into the brain as quantitatively detected by ultraviolet spectrophotometry (n=3).

As can be seen from the results shown in FIG. 26 and FIG. 27, as compared with the control group of Parkinson's disease, after the Axitinib and levodopa treatments, the amount of Evans blue permeated into the brain is reduced to varied degrees. However, the amount of Evans blue permeated into the brain in the Axitinib treatment group was significantly lower than that of the levodopa treatment group. It indicates that Axitinib can reduce blood-brain barrier permeability and promote recovery of a blood-brain barrier function from a pathologically impaired state to a state close to a physiological barrier with an efficacy superior to levodopa.

2-2 Dyskinesia in Parkinson's Disease is Significantly Improved after the Axitinib Treatment After the Axitinib treatment and the levodopa treatment was accomplished, movement time within 2 minutes (walking, lifting of both forelimbs, washing face, hair grooming and the like) was recorded for each of the test groups. The results were shown in FIG. 28.

Figure 28:
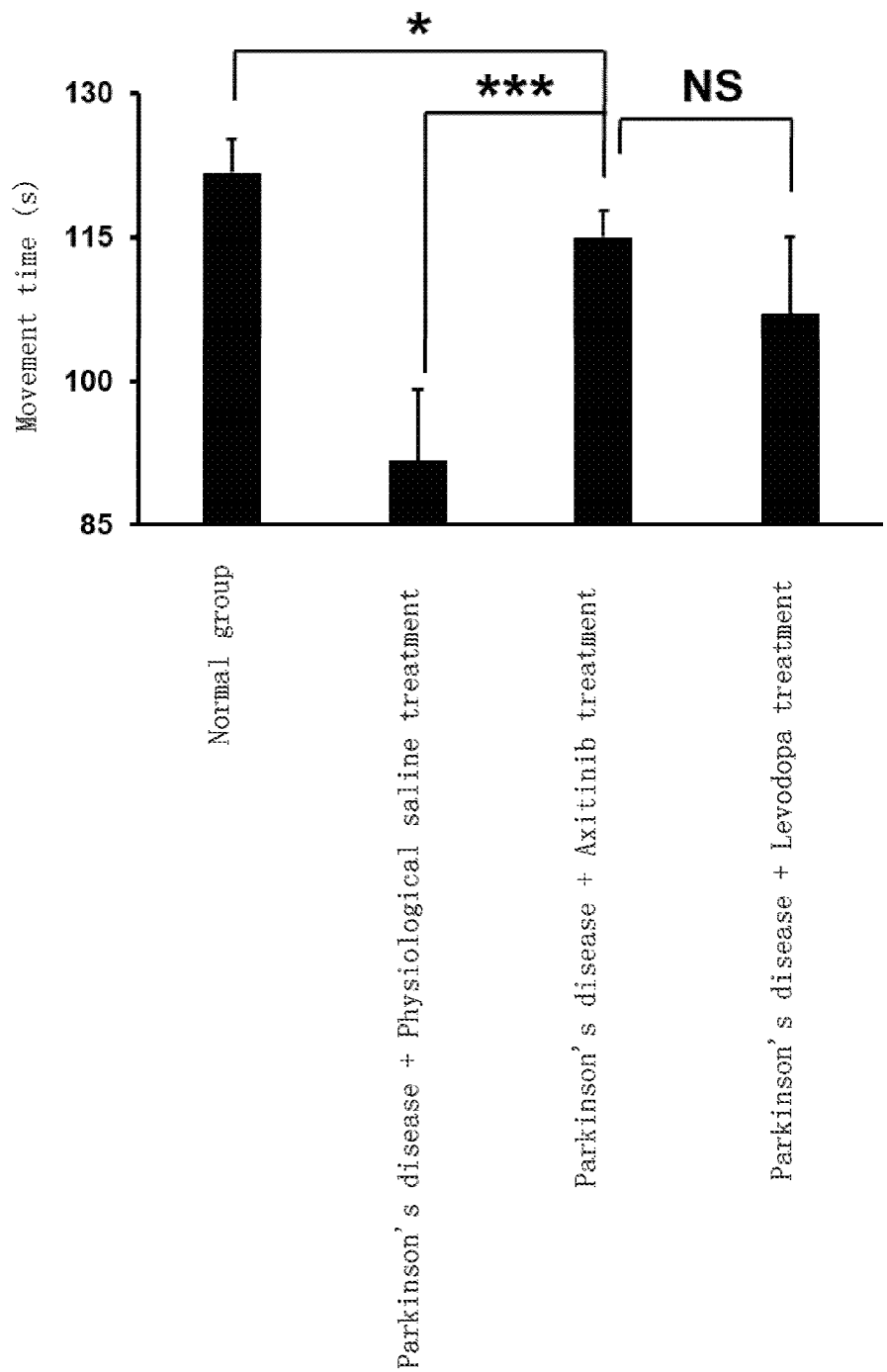
FIG. 28: Treatment of Parkinson's disease by regulating blood-brain barrier permeability by Axitinib, and recording of movement time of model animals. Male C57/BL6 (6-8 w) mice were used as model animals. A model of Parkinson's disease was established by stimulus of administration of 1-methyl-4-phenyl-1,2,3,6-tetrahydropyridine. Axitinib was injected into model animals of Parkinson's disease in tail veins at an administration dose of 10 mg/kg for 7 consecutive days. Levodopa dissolved in physiological saline was injected intraperitoneally at an administration dose of 20 mg/kg for 10 consecutive days. After the treatment was accomplished, movement time within 2 minutes (walking, lifting of both forelimbs, washing face, hair grooming and the like) was recorded for each of the test groups (n=5).

As can be seen from the results shown in FIG. 28, as compared with a control of Parkinson's disease, after the Axitinib treatment and the levodopa treatment, dyskinesia of model animals of Parkinson's disease can be both significantly alleviated. Both drugs show no difference in their efficacy.

2-3 Expression Level of Tyrosine Hydroxylase is Significantly Increased after the Axitinib Treatment After the treatment, the intact brain of the nude mice was taken by cardiac perfusion, and fixed with a 4% paraformaldehyde solution. After paraffin-embedding, a section of the coronal surface of the striatum of the brain tissue was taken with a thickness of 3 microns. An ascorbic acid buffer was applied to repair the tissue surface antigens. The sections were incubated with tyrosine hydroxylase primary antibody (1:1000 dilution) at 4° C. for 24 hours, and then were incubated with biotinylated secondary antibody (1:200 dilution) at 37° C. for 45 minutes, and then were incubated with streptavidin-horseradish peroxidase at 37° C. for 30 minutes. Development was performed with a DAB working solution. Expression of tyrosine hydroxylase in the section tissue was observed with an optical microscope. The results were shown in FIG. 29.

Figure 29:
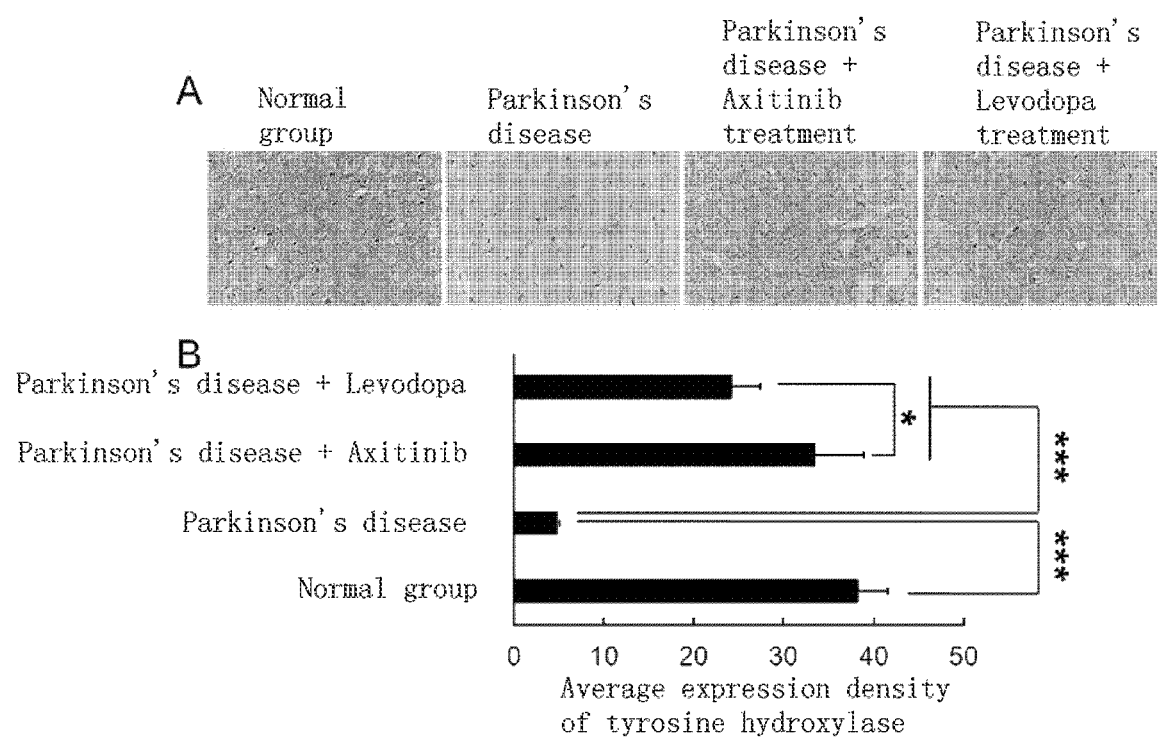
FIG. 29: Treatment of Parkinson's disease by regulating blood-brain barrier permeability by Axitinib, and expression of tyrosine hydroxylase in the brain tissue of model animals. Male C57/BL6 (6-8 w) mice were used as model animals. A model of Parkinson's disease was established by stimulus of administration of 1-methyl-4-phenyl-1,2,3,6-tetrahydropyridine. Axitinib was injected into model animals of Parkinson's disease in tail veins at an administration dose of 10 mg/kg for 7 consecutive days. Levodopa dissolved in physiological saline was injected intraperitoneally at an administration dose of 20 mg/kg for 10 consecutive days. After the treatment was accomplished, the intact brain of the nude mice was taken by cardiac perfusion, fixed with a 4% paraformaldehyde solution. After paraffin-embedding, a section of the coronal surface of the striatum of the brain tissue was taken, and then immunohistochemically stained with tyrosine hydroxylase. Panel A shows the results of expression of tyrosine hydroxylase in the brain tissue for each of test groups as observed by an optical microscope. Panel B is the semi-quantitative analysis results of expression of tyrosine hydroxylase by Image J (n=3).

As can be seen from the results shown in FIG. 29, Parkinson's disease may cause significant down-regulation of striatum tyrosine hydroxylase expression in the brain tissue. After the Axitinib treatment and the levodopa treatment, expression of striatum tyrosine hydroxylase in Parkinson's disease model animals can be both significantly up-regulated. The effect in the Axitinib treatment group was superior to that in the levodopa treatment group.

INDUSTRIAL APPLICABILITY

According to the present invention, a blood-brain barrier permeability regulator can be provided, which can reduce blood-brain barrier permeability, and promote recovery of a blood-brain barrier function from a pathologically impaired state to a state close to a physiological barrier, and thereby achieve a therapeutic effect on a disease related to inducing of a change in blood-brain barrier permeability through the regulation of Axitinib and analogs thereof on blood-brain barrier permeability. Therefore, the present invention has great applicability in the field of medicine.

The invention claimed is:

1. A method for regulating blood-brain barrier function, comprising administering to a subject with glioma Axitinib at an administration dose of about 10 mg/kg, wherein Axitinib is administered as a sole agent for only 7 consecutive days, and wherein prior to and subsequent to Axitinib treatment the subject is not treated with any other agent.

2. The method of claim 1, wherein the Axitinib reduces blood-brain barrier permeability and promotes recovery of a blood-brain barrier function from a pathologically impaired state to a state close to a physiological barrier.

3. The method of claim 1, wherein the Axitinib reduces blood-brain barrier permeability by reducing the degree to which a pathological blood-brain barrier tight junction protein Claudin-5/Occludin is down-regulated.

4. The method of claim 1, wherein the Axitinib reduces blood-brain barrier permeability by inhibiting a vascular endothelial cell growth factor-phosphatidylinositol kinase-protein kinase B signaling pathway and reducing the degree to which a blood-brain barrier tight junction protein Claudin-5/Occludin is down-regulated.

5. A method for treating a disease related to inducing a change in blood-brain barrier permeability in a subject with glioma and in need of treatment, comprising administering to the subject with glioma Axitinib at an administration dose of about 10 mg/kg, wherein Axitinib is administered a sole agent to the subject having glioma for only 7 consecutive days, and wherein prior to and subsequent to Axitinib treatment the subject is not treated with any other agent.

6. The method of claim 1, wherein the Axitinib is administered to the subject at a concentration of 0.5~20 µg/mL.

* * * * *